United States Patent
Scheucher et al.

(10) Patent No.: US 9,885,646 B2
(45) Date of Patent: Feb. 6, 2018

(54) GAS MEASUREMENT APPARATUS

(71) Applicant: Solon Manufacturing Company, Chardon, OH (US)

(72) Inventors: Karl F. Scheucher, Waite Hill, OH (US); Perry Blossom, Chardon, OH (US); George Davet, Chardon, OH (US)

(73) Assignee: Solon Manufacturing Company, Chardon, OH (US)

( * ) Notice: Subject to any disclaimer, the term of this patent is extended or adjusted under 35 U.S.C. 154(b) by 0 days.

(21) Appl. No.: 14/996,124

(22) Filed: Jan. 14, 2016

(65) Prior Publication Data

US 2016/0209310 A1    Jul. 21, 2016

Related U.S. Application Data

(60) Provisional application No. 62/103,958, filed on Jan. 15, 2015, provisional application No. 62/271,142, filed on Dec. 22, 2015.

(51) Int. Cl.
  *G01N 9/26* (2006.01)

(52) U.S. Cl.
  CPC .................... *G01N 9/266* (2013.01)

(58) Field of Classification Search
  CPC .................... G01N 9/26; G01N 9/266
  See application file for complete search history.

(56) References Cited

U.S. PATENT DOCUMENTS

| | | | |
|---|---|---|---|
| 3,046,369 A | 7/1962 | Hicks | |
| 3,749,865 A | 7/1973 | Kalt et al. | |
| 4,364,271 A | 12/1982 | Froome | |
| 5,245,869 A | 9/1993 | Clarke | |
| 5,881,779 A * | 3/1999 | Kountz | F17C 5/06 141/2 |
| 6,205,846 B1 * | 3/2001 | Dupraz | H01H 33/563 340/605 |
| 7,149,374 B2 | 12/2006 | Lagakos et al. | |

(Continued)

FOREIGN PATENT DOCUMENTS

| | | |
|---|---|---|
| CN | 1987412 A | 6/2007 |
| CN | 201653851 U | 11/2010 |
| WO | 2010/043268 A1 | 4/2010 |

OTHER PUBLICATIONS

International Search Report for Intl. App. No. PCT/US2016/013472, dated Apr. 29, 2016.

(Continued)

*Primary Examiner* — Harshad R Patel
*Assistant Examiner* — Punam Roy
(74) *Attorney, Agent, or Firm* — BakerHostetler LLP

(57) ABSTRACT

Systems and methods for calculating gas densities within a fluid enclosure are disclosed. In an example embodiment, a system includes a temperature probe for measuring an enclosure temperature in a fluid enclosure filled at least in part with a fill gas, an atmospheric pressure sensor for measuring the atmospheric pressure outside the fluid enclosure, a gas sensor for measuring an enclosure pressure within the fluid enclosure, and a controller for calculating a fill gas density within the fluid enclosure based at least in part on the enclosure temperature, the atmospheric pressure, the enclosure pressure, and a gas coefficient of the fill gas.

2 Claims, 27 Drawing Sheets

(56) References Cited

U.S. PATENT DOCUMENTS

| | | | |
|---|---|---|---|
| 7,249,517 | B2 | 7/2007 | Heuer et al. |
| 9,212,966 | B2 | 12/2015 | Scheucher |
| 9,222,620 | B2* | 12/2015 | Harty ............... F17C 5/007 |
| 9,347,614 | B2* | 5/2016 | Mathison ............ F17C 5/06 |
| 9,362,071 | B2* | 6/2016 | Boucher ........... H01H 33/26 |
| 2010/0063749 | A1 | 3/2010 | Kurtz |
| 2011/0259469 | A1* | 10/2011 | Harty ............... F17C 5/007 141/4 |
| 2012/0306656 | A1* | 12/2012 | Boucher .......... H01H 33/563 340/638 |
| 2012/0329166 | A1 | 12/2012 | Skarping et al. |
| 2013/0031958 | A1* | 2/2013 | Scheucher ......... G01M 3/002 73/31.05 |
| 2014/0000342 | A1 | 1/2014 | Downie |
| 2014/0224770 | A1 | 8/2014 | Hensberger et al. |
| 2015/0355049 | A1* | 12/2015 | Ait Abdelmalek .. H01H 33/563 702/45 |

OTHER PUBLICATIONS

United States Environmental Protection Agency, "Inventory of U.S. Greenhouse Gas Emissions and Sinks: 1990-2008", Washington, DC, Apr. 15, 2010, Available at http://www.epa.gov/climatechange/emissions/downloads10/US-GHG-Inventory-201 O_Report.pdf.

Debra Knopman, Katie Smythe, "2004-2006 SF6 Data Summary", PM-2327-NEMA, Jun. 2007, Prepared for the National Electrical Manufacturers Association, Available at http://www.epa.gov/electricpower-sf6/documents/04-06_data_summary.pdf.

United States Environmental Protection Agency, "SF6 Emission Reduction Partnership for Electric Power Systems 2007 Annual Report", Washington, DC, Dec. 2008, Available at http://www.epa.gov/electricpower-sf6/documents/sf6_2007_ann_report.pdf.

Jos Olivier, Joost Bakker, Jan Willem Wouda, Rainer Bitsch, and Manfred Maiss, "Global Emission Sources of Greenhouse Gas Emissions from Industrial Processes: SF6", IPCC Task Force on National Greenhouse Gas Inventories, Jan. 2003, Available at <http://www.ipcc-nggip.iges.or.jp/public/gp/bgp/3_9_Global_Sources_Industrial_Processes_SF6.pdf.

L. G. Christophorou, J. K. Olthoff, and D. S. Green, "Gases for Electrical Insulation and Arc Interruption: Possible Present and Future Alternatives to Pure SF6", NIST Technical Note 1425, Nov. 1997, Available at <http://www.epa.gov/electricpower-sf6/documents/new_report_final.pdf.

United States Environmental Protection Agency, "Electric Transmission and Distribution Equipment Use—Final Rule: Mandatory Reporting of Greenhouse Gases (40 CFR 98, Subpart DD)", Nov. 2010, Available at <http://www.epa.gov/climatechange/em issions/downloads 1O/Subpart-DD_infosheet.pdf.

Alfieri, M. 2002. "Partner Case Study: Con Edison", Presented on behalf of Con Edison at the International Conference on SF6 and the Environment: Emission Reduction Strategies. San Diego, CA, Nov. 21-22, 2002. Available at <http://www.epa.gov/highgwp1/sf6/proceedings/agenda.html.

Robert Madding and Robert Benson, "Detecting SF6 Insulating Gas Leaks with an IR Imaging Camera", Electricity Today, pp. 12-15, Nov./Dec. 2007, Available at <http://www.electricity-today.com/et/issue0907/ir_camera.pdf.

Jan-Martin Rhiemenier, Sina Wartmann, Marcello Pagnotta, Natalia Makowska, and Xingyu Li, "Update on global SF6 Emissions trends from electrical equipment—Edition 1.1", Ecofys Germany GmbH, Jul. 2010, Available at <http://www.ecofys.com/com/pub lications/brochures_newsletters/documents/ES I-SF6_Final-report_edition11_100701_vO1 . pdf.

U.S. Department of Energy, "U.S. Energy Information Administration Electric Power Annual 2009", Washington, DC, Nov. 2010, Available at <http://www.eia.gov/cneaf/electricity/epa/epa_sum.html>.

Wika Alexander Wiegand GmbH & Co. KG, "Gas Density Monitor (GDM) with Integrated Gas Density Transmitter, Model 233.52.100 TI", Klingenberg, Germany, May 2009, Available at <http://en-co.wika.de/upload/DS_SP6005_GB_7922.PDF.

J. Blackman, M. Averyt, and Z. Taylor, "SF6 Leak Rates from High Voltage Circuit Breakers—U.S. EPA Investigates Potential Greenhouse Gas Emissions Source", presented at the International Conference on SF6 and the Environment: Electric Power Systems—Partnership Update, Nov. 28, 2006, Available at <http://www.epa.gov/electricpower-sf6/documents/leakrates_circuitbreakers.pdf.

General Electric Company, "72.5kV Circuit Breakers Data Sheet", Nov. 10, 1999, Available at <http://www.geindustrial.com/publibrary/checkout/72.5DAT?TNR=Data%20SheetsI72.5DATIPDF.

General Electric Company, "121kV Circuit Breakers Data Sheet", Mar. 1, 2002, Available at <http://www.geindustrial.com/publibrary/checkout/121 DATA?TNR=Data%20SheetsI 121DATAIPDF.

General Electric Company, "145kV Circuit Breakers Data Sheet", Nov. 10, 1999, Available at <http://www.geindustrial .com/publibrary/checkout/Data%20SheetsI 145DATAI PDF.

General Electric Company, "169kV Circuit Breakers Data Sheet", Nov. 10, 1999, Available at <http://www.geindustrial .com/publibrary/checkout/Data%20SheetsI 169DATAI PDF.

General Electric Company, "242kV Circuit Breakers Data Sheet", Nov. 10, 1999, Available at <http://www.geindustrial .com/publibrary/checkout/Data 0/o20SheetsI242DA TAI PDF.

General Electric Company, "362kV Circuit Breakers Data Sheet", Nov. 10, 1999, Available at <http://www.geindustrial .com/publibrary/checkout/Data%20SheetsI362DA TA5 lPDF.

General Electric Company, "550kV Circuit Breakers Data Sheet", Nov. 10, 1999, Available at <http://www.geindustrial .com/publibrary/checkout/Data%20SheetsI550DA TA41PDF.

Solon Manufacturing Company, "2TC, SF Gas Density Switch, Intrinsic Gauge Design", Chardon, OH, Available at <http://www.solonmfg.com/controls/techdocs/documents/2tcspec.pdf.

Giancarlo Scalabrin, Luigi Bettio, Paolo Marchi, and Paolo Stringari, "A Fundamental Equation of State for Sulfur Hexaftuoride (SF6) in Extended Equation of State Format", JPCRD 36(2) pp. 617-662, 2007, Available at <http://energyfromthorium.com/forum/download/file.php?id=44 &sid=275692ae3353e590221e1226f0501ac1.

Maryland Department of the Environment, "Maryland C02 Budget Trading Program, COMAR 26.09.03", Baltimore, MD, Aug. 2009, Available at <http://www.mde.state.md.us/programs/Air/RGGI/Documents/www.mde.state.md.us/assets/document/air/RGGI/04_SF6_0ffset_FINAL.pdf.

California Environmental Protection Agency, Air Resources Board, "Proposed Regulation Order: Regulation for Reducing Sulfur Hexaftuoride Emissions from Gas Insulated Switchgear", Sacramento, CA, Jan. 7, 2010, Available at <http://www.arb.ca.gov/regacl/2010/sf6elec/appa.pdf.

United Nations Framework Convention on Climate Change, "SF6 Emission Reductions in Electrical Grids", Bonn, Germany, Sep. 29, 2006, Available at <http://cdm.unfccc.int!filestorage/CDMWF_AM_5WABPI8CK9HOSTV8E9CKDPFZM7UKQU/EB26_repan 02_AM0035_NM0135_pdf?t=ekZ8MTI5MTM5NDM5NS45 NA==i3FfpdD3nIBJADrv6dXLw5eW37cE=.

United States Department of the Interior Bureau of Reclamation, "Management and Safe Handling Procedures for Sulfur Hexaflouride (SF6) Gas", Mar. 2004, Available at <http://www.usbr.gov/power/data/fisl/fist5_9/fist5_9.pdf.

International Search Report in PCT/US2016/013472 dated Jul. 27, 2017.

* cited by examiner

GAS MEASUREMENT APPARATUS

CROSS-REFERENCE TO RELATED APPLICATIONS

This patent application claims priority to and the benefit of provisional patent applications 62/103,958 filed Jan. 15, 2015 and 62/271,142 filed Dec. 22, 2015, both of which are incorporated herein by reference in, their entirety.

TECHNICAL FIELD

The subject innovation generally relates to gas measuring equipment. The subject innovation more specifically concerns electronically monitored gas measuring equipment.

BACKGROUND

Various techniques exist for measuring gases (as well as liquids and other material) and for determining the concentration or pressure of such in a given space. Different techniques among these can work with varying reliability or accuracy based on the location of sensors and their ability to accurately reflect the systemic variables as opposed to a point-value. Further, while sensors may provide instantaneous data relating to the measured gases, such data does not provide insight into past trends or future values.

SUMMARY

In an embodiment, an apparatus comprises a temperature probe that receives at least an enclosure temperature from a fluid enclosure, the fluid enclosure filled at least in part with a fill gas, an atmospheric pressure sensor that receives at least an atmospheric pressure, a gas sensor that receives at least an enclosure pressure within the fluid enclosure, and a controller configured to compute a fill gas density within the fluid enclosure based at least in part on the enclosure temperature, the atmospheric pressure, the enclosure pressure, and a gas coefficient of the fill gas.

In another embodiment, a method includes measuring an enclosure temperature in a fluid enclosure filled at least in part with a fill gas, measuring an atmospheric pressure outside the fluid enclosure, measuring an enclosure pressure within the fluid enclosure, and calculating a fill gas density within the fluid enclosure based at least in part on the enclosure temperature, the atmospheric pressure, the enclosure pressure, and a gas coefficient of the fill gas.

In another embodiment, a system includes means for measuring an enclosure temperature in a fluid enclosure filled at least in part with a fill gas, means for measuring an atmospheric pressure outside the fluid enclosure, means for measuring an enclosure pressure within the fluid enclosure, and means for calculating a fill gas density within the fluid enclosure based at least in part on the enclosure temperature, the atmospheric pressure, the enclosure pressure, and a gas coefficient of the fill gas.

These and other embodiments are described in greater detail below.

BRIEF DESCRIPTION OF THE DRAWINGS

The invention may take physical form in certain parts and arrangements of parts, an embodiment of which will be described in detail in the specification and illustrated in the accompanying drawings which form a part hereof, and wherein.

DETAILED DESCRIPTION OF ILLUSTRATIVE EMBODIMENTS

Figure 1A:
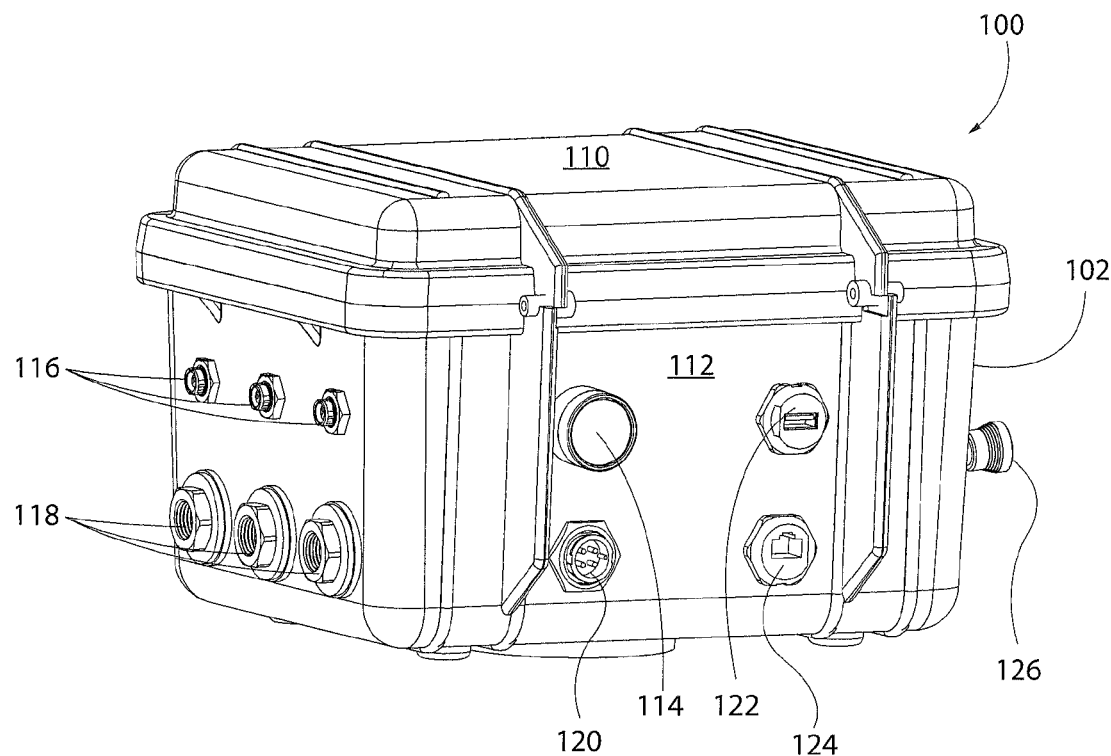
FIGS. 1A and 1B illustrate an example sensor for monitoring fluids.

Embodiments concern techniques for monitoring fluid in enclosures, and specifically for monitoring gas density in enclosures. Further embodiments include apparatuses for monitoring gas density in enclosures. Still further embodiments include techniques and apparatuses for automatically changing fluid levels (e.g., gas density) in an enclosure based on monitored values.

As used herein, a "fluid enclosure" is a substantially fluid-impermeable enclosure containing a measurable fluid. The measurable fluid can be a gas. As used herein, a "fill gas" is a gas comprising at least a portion of the fluid in a fluid enclosure. The fluid enclosure has an enclosure temperature (e.g., the systemic or aggregate temperature of the fluid(s) and possibly other material contained therein), an enclosure pressure, as well as various densities to include a fill gas density which quantifies the gas density of the fill gas in the fluid enclosure. An external temperature and atmospheric pressure are values taken outside the fluid enclosure and generally refer to ambient values. A "step" herein is a change in value deviating from trends. For example, a slow leak is not a step, but rather a gradient. A step, on the other hand, can include (but is not limited to) a significant refilling of a gas enclosure over a short period of time or a significant failure releasing gas from the gas enclosure over a short period of time (resulting in one or both of a pressure step and a gas density step). Controllers herein can, but need not, be comprised of all modules typically found in computing devices, including but not limited to programmable logic controllers and/or circuit boards. In embodiment a controller is a computer module; in alternative embodiments a controller is one or more circuits specifically designed to effect functions described herein. "Thresholds" such as gas fill thresholds are described hereafter in various examples, but can include (without being limited to) alarm values, lockout values, fill values (or fill target values), overpressure values, standoff values above or below those listed, or other preprogrammed values calculated or arbitrarily provided. Specifically, a fill gas threshold is a density or pressure value related to at least one gas filling a fluid enclosure. The meaning(s) of other terms herein will be understood based on their usage and knowledge of the art.

A variety of variables impact a gas sensor's ability to measure gas density in a fixed volume tank. Temperature, one such variable, can vary over the course of a day and can change dramatically over time in certain climates. More, temperature can vary at different locations within or on edges of the fixed volume. Significant temperature gradients can arise due to asymmetric heating or cooling. Such asymmetric effects can be due to, e.g., differing exposure to wind, sun, and precipitation. This can complicate positioning of temperature probes inasmuch as reliable, accurate reflections of gas temperature can be challenging to produce.

The consequence of temperature discrepancies is understood through physics and more specifically the ideal gas law, which dictates that, in a fixed volume, pressure will vary directly with temperature. However, because pressure can also be monitored, discrepancies will exist as to the amount of substances in the fixed volume based on temperature discrepancies. Density estimate discrepancies can result. For example, when the actual gas temperature is above the measured temperature value, such as can occur when ambient temperature outside the fixed volume is falling, density can be overestimated. In a similar example, when the actual gas temperature is below the measured temperature value, such as can occur when ambient temperature outside the fixed volume is rising, density can be underestimated.

Figure 1B:
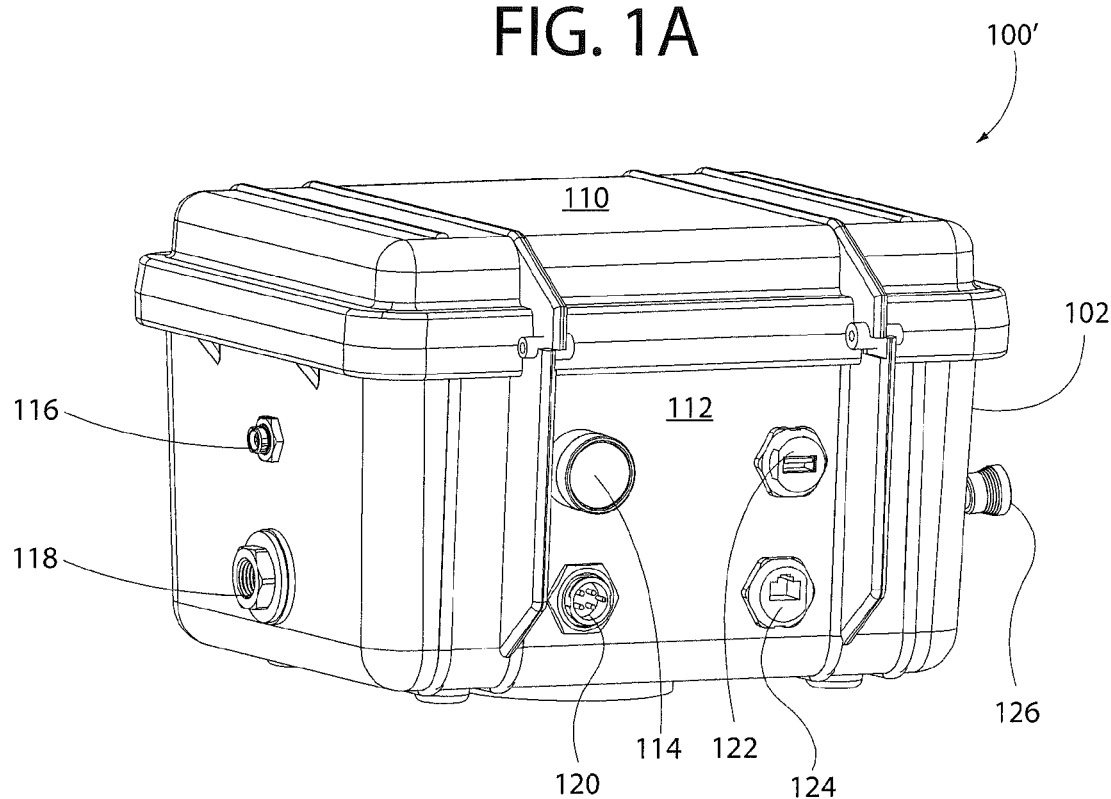
Figure 2:
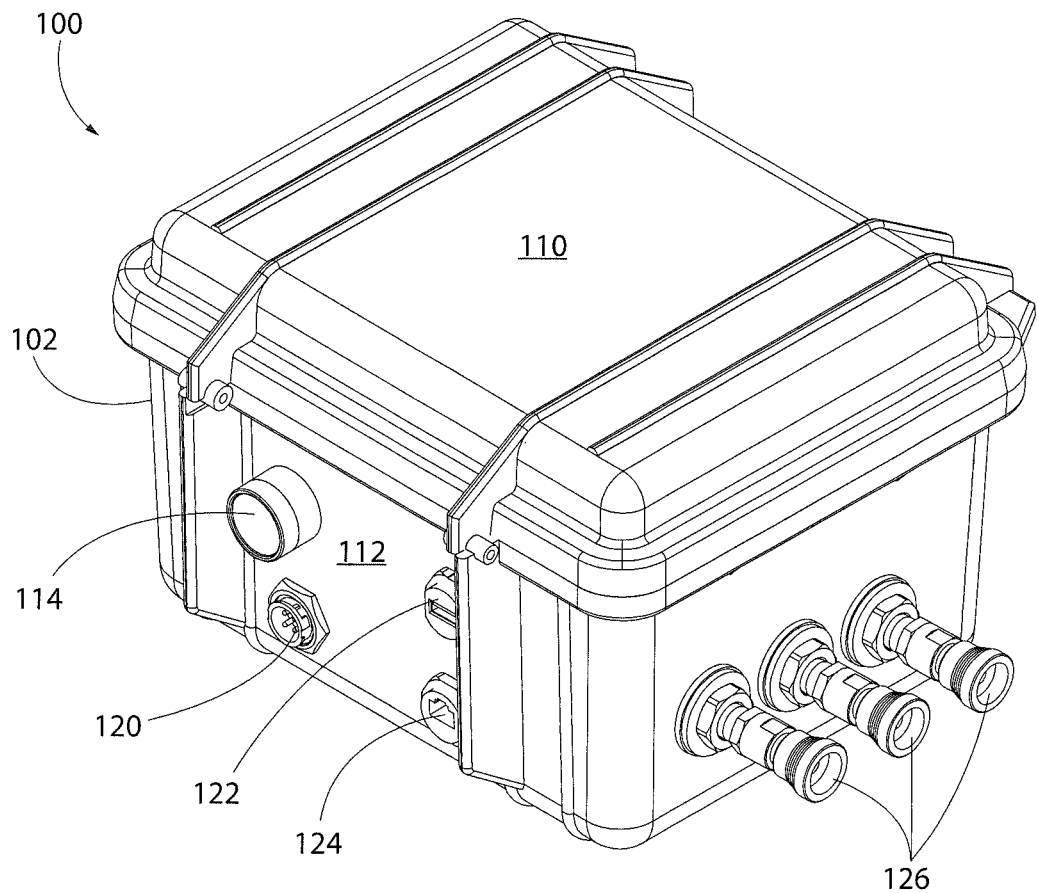
FIG. 2 illustrates another view of an example sensor for monitoring fluids.
Figure 3:
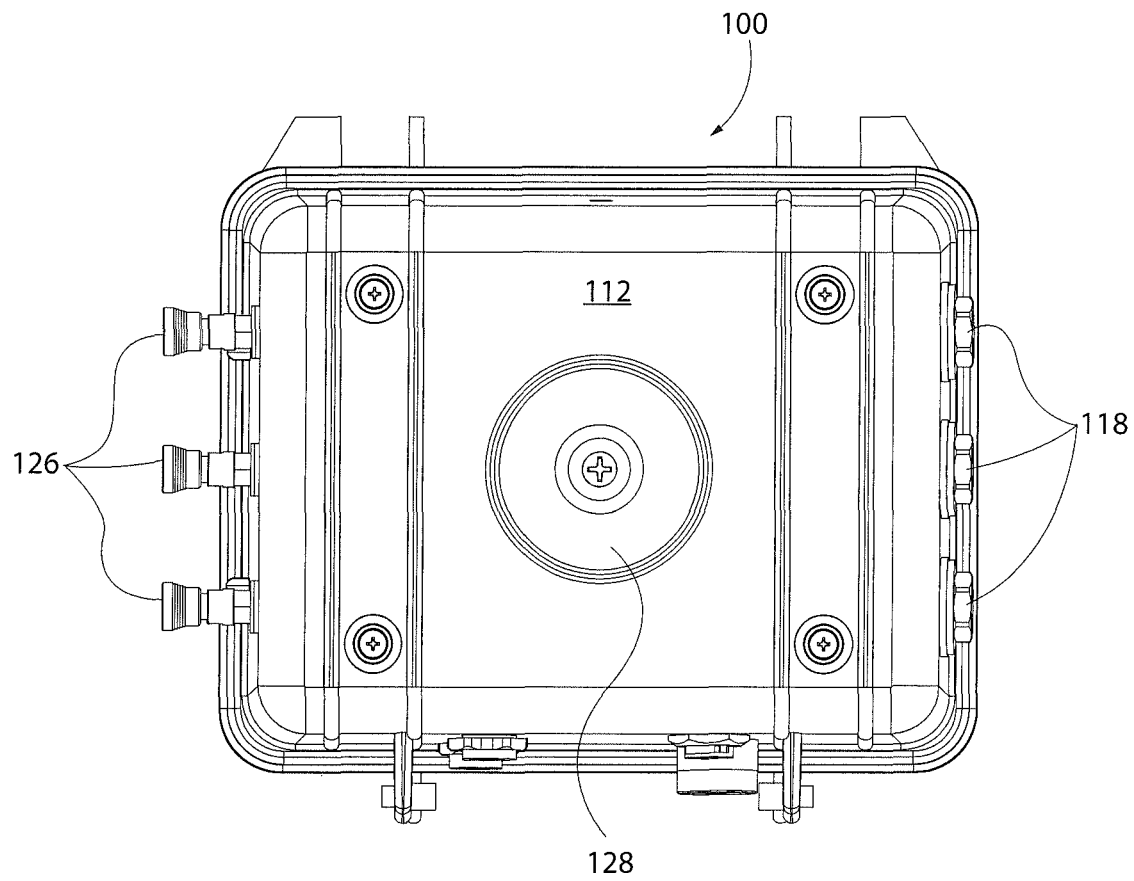
FIG. 3 illustrates another view of an example sensor for monitoring fluids.

The innovations herein address these and other issues. In this regard, FIGS. 1A, 2, and 3 illustrate a fluid monitoring device 100, and FIG. 1B illustrates an alternate fluid monitoring device 100'. Fluid monitoring device 100 can monitor, e.g., the fluid in an enclosure such as a circuit breaker. The fluid monitored can include pure gas, gas mixes, or selectable gas combinations. The elements of fluid monitoring device 100 may be contained within or attached to a case 102 or other suitable housing or frame. In the example shown, case 102 includes a case body 112 that defines a space for receiving components therein. The case body 112 includes one or more walls that outline an interior space. The space may be accessible by removable panels or disassembly of the case or as shown, case 102 may include an openable top 110 hingedly attached to body 112.

At least case body 112 is adapted to accept various ports and components. For example, components may be mounted directly to a wall or surface of case 102 including case body 112 or top 110. Alternatively, components may be supported on case indirectly through brackets designed to fit within case 102 or attach to case 102. Openings in case 102 may be provided to attach external components to the components within the case. Since the case 102 is generally located outdoors, it may be constructed to be weather resistant and include seals at the top 110 and at the various ports or other openings formed in the case to seal the interior of case 102.

The case may include a variety of ports and can include, for example, indicator-actuator 114, temperature probe port 116, auxiliary port 126, power port 120, network port 124, local data port 122, and gas test port 118. It will be understood that case 102 may have only the ports required for a particular embodiment with the other ports omitted. Or the case may include additional ports that allow the user to change the functionality of fluid monitoring device 100 by attaching/detaching components as needed.

Indicator-actuator 114 can be a backlit button or other control providing the capability to initiate activity in fluid monitoring device 100 as well as visual feedback for initiation of fluid monitoring device 100 and indication of its status.

Temperature probe port 116 can include one or more ports for receiving data from temperature probes. Such temperature probes can be located in or around the fluid enclosure being monitored. These ports can receive digital or analog data from the temperature probes to discern the temperature within the fluid enclosure, and in embodiments, on the surfaces or outside the fluid enclosure. Temperature probe port 116 can be adapted to accept a remote thermistor or other temperature sensor.

Auxiliary port 126 may be provided for various purposes. In embodiments, auxiliary port 126 can provide fluid communication with elements of fluid monitoring device 100 to facilitate connecting or chaining multiple devices, testing fluid monitoring device 100 while it is operating, monitoring multiple tanks (or multiple phases of a single fluid enclosure) with one device, connecting a gas source to indirectly push gas into systems connected to fluid monitoring device 100, or other purposes. In embodiments, no auxiliary port 126 is included.

Power port 120 can be configured to accept a power cord, battery, or other device for providing electrical power to operate fluid monitoring device 100. Network port 124 accepts at least one cable for connecting device 100 to a network. When connected to a network, device 100 can provide data related to monitored levels and calculated information for storage or display, send or receive instructions or data to electronics associated with monitored fluid enclosures or other devices, and/or receive instructions for operation or control from a remote operator or master device. Local data port 122 can be a port for connecting local devices or storage (e.g., a universal serial bus port) to allow information to be transferred to or from device 100 to a locally attached device. In embodiments, a wireless data port can replace or supplement network port 124 and/or local data port 122 to provide wireless communication with remote electronics.

Gas test port 118 receives gas samples from the monitored fluid enclosure for analysis. In embodiments, gas test port 118 can include or be coupled with diagnostic equipment to produce digital or analog signals representing gas quantities about the gas including but not limited to pressure, gas density, et cetera. In a specific embodiment, gas test port 118 produces at least an enclosure gas pressure signal.

Fluid monitoring device 100 can further include or be operatively coupled with additional sensors or ports, or leverage the ports described above for additional functionality. Such sensors and ports can include an atmospheric pressure sensor.

Case body 112 may optionally be provided with a mounting device to facilitate mounting of fluid monitoring device 100 in the field. The mounting device may include a suitable fastener, hanger or bracket that attaches to a structure. In the embodiment shown, mounting device is a magnet 128 that supports the case on a metal structure. Magnet 128 can be used for positioning or mounting fluid monitoring device 100 in a removable manner proximate to fluid enclosures for monitoring.

While the various ports and components are shown in combinations on specific sides or faces of case body 112, it is appreciated that other configurations and combinations can be utilized without departing from the scope or spirit of the innovation. FIGS. 1A and 1B illustrate use of different numbers of ports (e.g., three gas input ports or one gas input port; three temperature ports or one temperature port; three gas test ports or different numbers of gas test ports) can be utilized in different embodiments depending on the application. In embodiments having duplicate ports, such duplicate ports can be used for redundantly monitoring a single gas enclosure, monitoring multiple points or sample areas of a single gas enclosure, monitoring two or more gas enclosures (using one or more sensors per enclosure), et cetera. Further, certain ports can be excluded altogether in embodiments without interfering with the operation of fluid monitoring device 100. The various ports and components can further be weatherproofed (e.g., provided with moisture barriers, insulating materials, et cetera) to ensure the integrity of components within case 102.

Based on the information detected, received, and processed, fluid monitoring device 100 can deliver a variety of displays or reports to a remote system (e.g., dedicated monitoring device or controller, web browser, mobile application, computer program). Such reports can include date and time information, location identifiers for fluid monitoring device 100 or associated fluid enclosures, name identifiers for fluid monitoring device 100 or associated fluid enclosures, system status, gas type, reference temperature, lockout threshold, alarm threshold, fill threshold (e.g., as a total pressure/density or as a step size), overpressure threshold, gas density, sample interval, time to alarm, time to lockout, liquefaction status, temperature corrected pressure, gauge pressure, atmospheric pressure, et cetera. Such data and reports generated from such data (e.g., by organizing and arranging the data in a display or page) can be provided using, e.g., network port 124, local data port 122, and/or other components.

Figure 4:
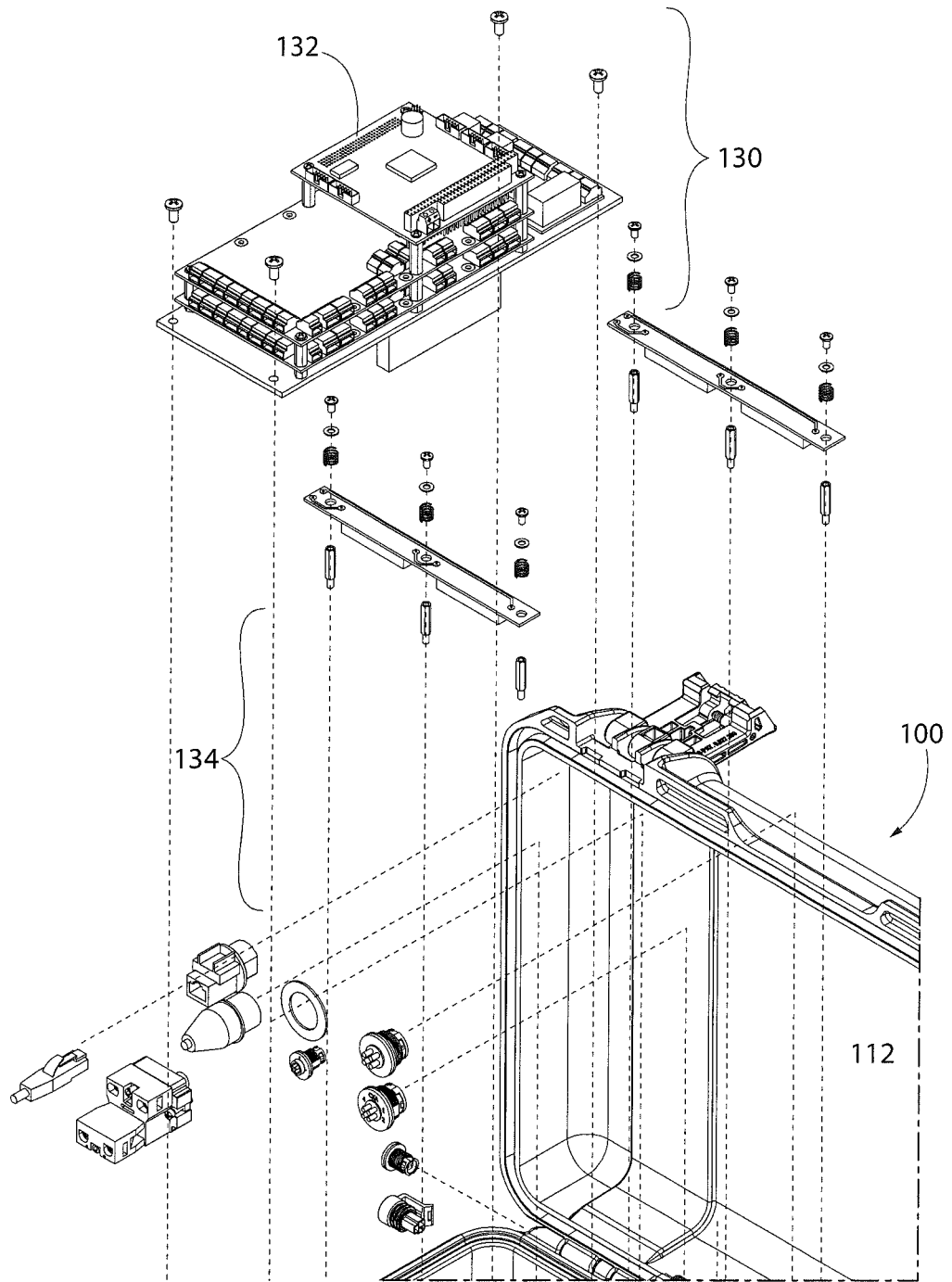
FIG. 4 illustrates components provided in an example sensor for monitoring fluids.

FIG. 4 illustrates internal assembly 130 including a controller 132 and installation hardware 134. Internal assembly 130 can include various sensors, converters, connectors, et cetera, to ensure variables can be measured, received, and/or converted, then provided as analog or digital signals, for transformation through calculation and reporting aspects described below.

Controller 132 can be configured to receive data from sensors, ports, or other components of fluid monitoring device 100. This data can be stored and/or processed using controller 132 and associated electrical or electronic components. Processing and transformation of the data received is described hereafter.

Further embodiments of the innovation concern fluid monitoring devices capable of auto-filling enclosures with fluid in response to fluid measurement information or calculations.

In specific embodiments, the fluid can be a gas in an enclosure (e.g., SF6 in a circuit breaker). While gas measurement information can include various aspects of composition, pressure, temperature, in a non-limiting embodiment a particular chemical density within the overall mix of chemicals in the gas can be a significant metric. For example, certain applications utilize particular gaseous chemicals to encourage or discourage certain behavior in a given space. A specific example is the use of sulfur hexafluoride as a dielectric to reduce or prevent arcing in high-voltage enclosures. When the concentration of the chemical falls below a certain level, the behavior becomes less predictable (or predictable in undesirable manners), and the concentration of the chemical should be increased. In this regard, it may not be necessary to increase pressure significantly (or at all) when concentrated units of the particular chemical are dosed into the overall mixture.

Thus, in an embodiment describing a gas measuring apparatus with auto-fill capability, the apparatus includes hardware and logic to accomplish several solutions. The apparatus maintains the proper density of one or more chemicals based on measured gas characteristics in reference to threshold levels or ranges. In this regard, the apparatus has the ability to fill a space (e.g., an energized circuit breaker) to the threshold level or range of concentration for safe operation. When installed, the apparatus can modify chemical density without taking associated equipment (e.g., the energized circuit breaker) offline, thereby avoiding downtime and improving safety. Further, because feedback regarding low density can be immediately actioned, lower overall gas densities and pressures can be maintained, thereby reducing the rate of leakage which is dependent upon the pressure difference between the inside and outside of the enclosure. When low levels are detected, the apparatus can dose gas at a predetermined rate or in discrete doses to prevent overfilling or waste. Further, when a dosing is completed, a notification can be transmitted, and amounts of gas added can be aggregated, stored, and reported. One or more dosing sources (e.g., external bottle, supply line, internal reservoir, others) can be monitored for level and an alert or report can be sent based on the available gas for dosing. The data recorded and reported can also be used to correct breaker nameplate capacity where the manufacturer's documented capacity differs from the actual capacity. The apparatus' measuring capabilities can be used to report gas leak rates and/or instances of leakage. The apparatus is portable can reconfigurable for attachment to different hardware such as breakers (e.g., semi- or non-permanent installation).

Figure 5:
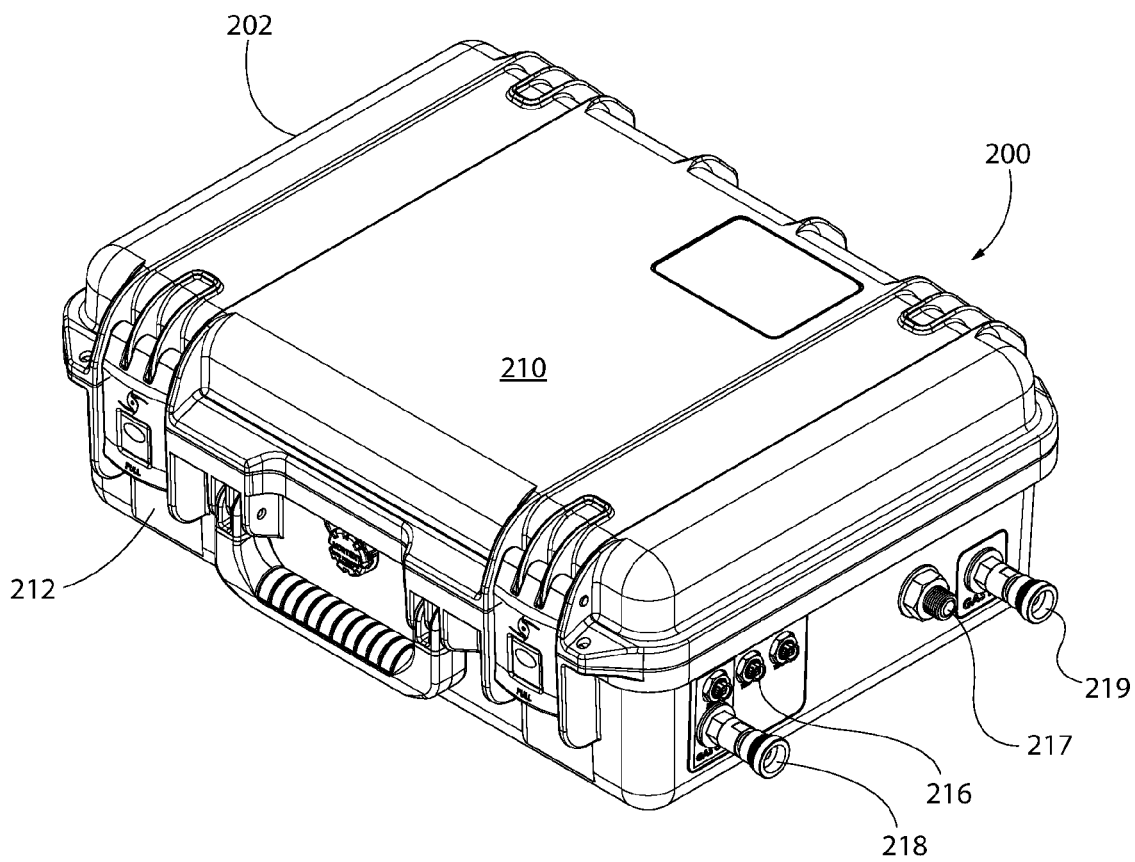
FIG. 5 illustrates an example embodiment of a fluid measurement apparatus with auto-fill capability.
Figure 6A:
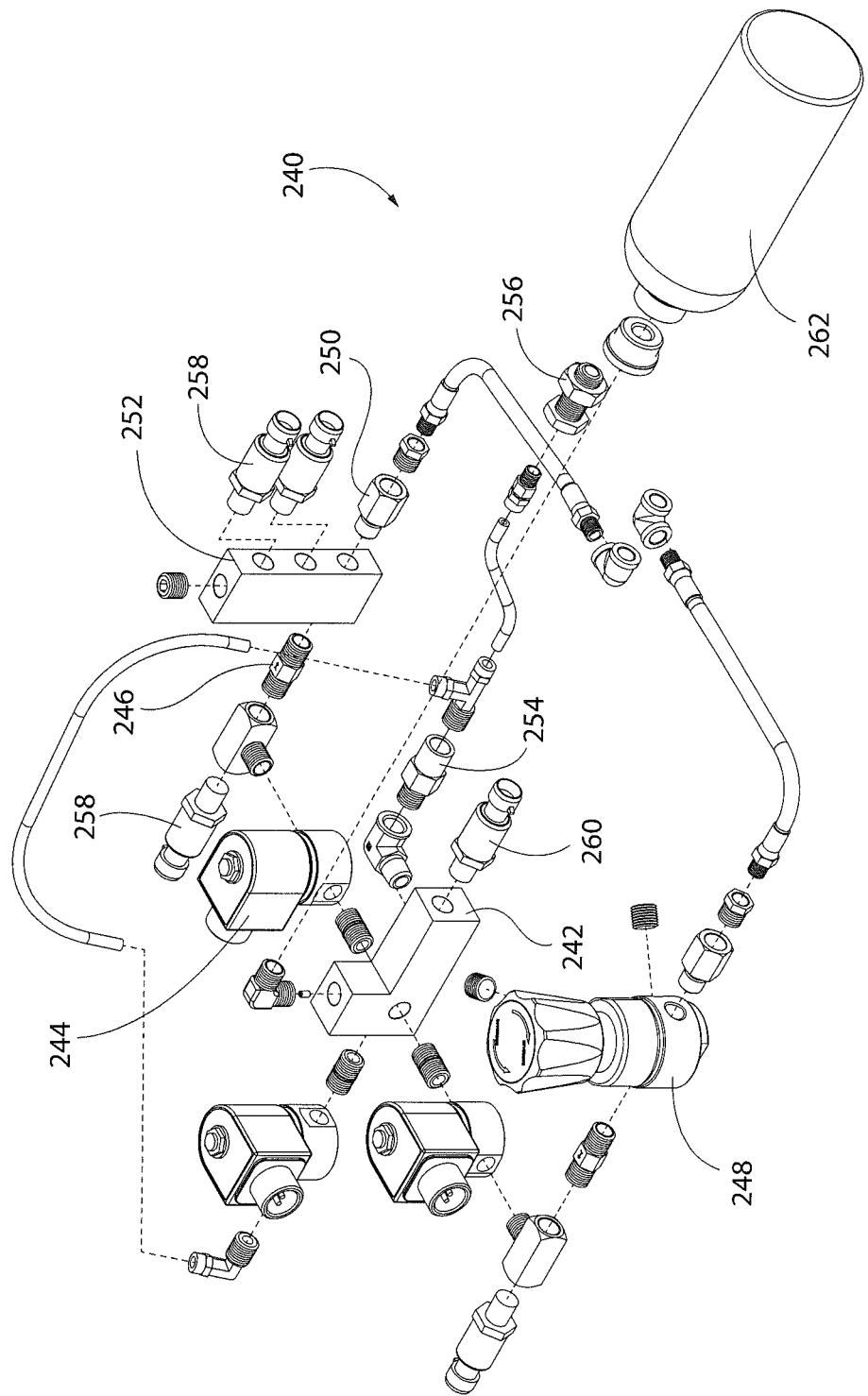
FIGS. 6A and 6B illustrate an example embodiment of an auto-fill sub-assembly for use with fluid measurement apparatuses such as those disclosed herein.
Figure 6B:
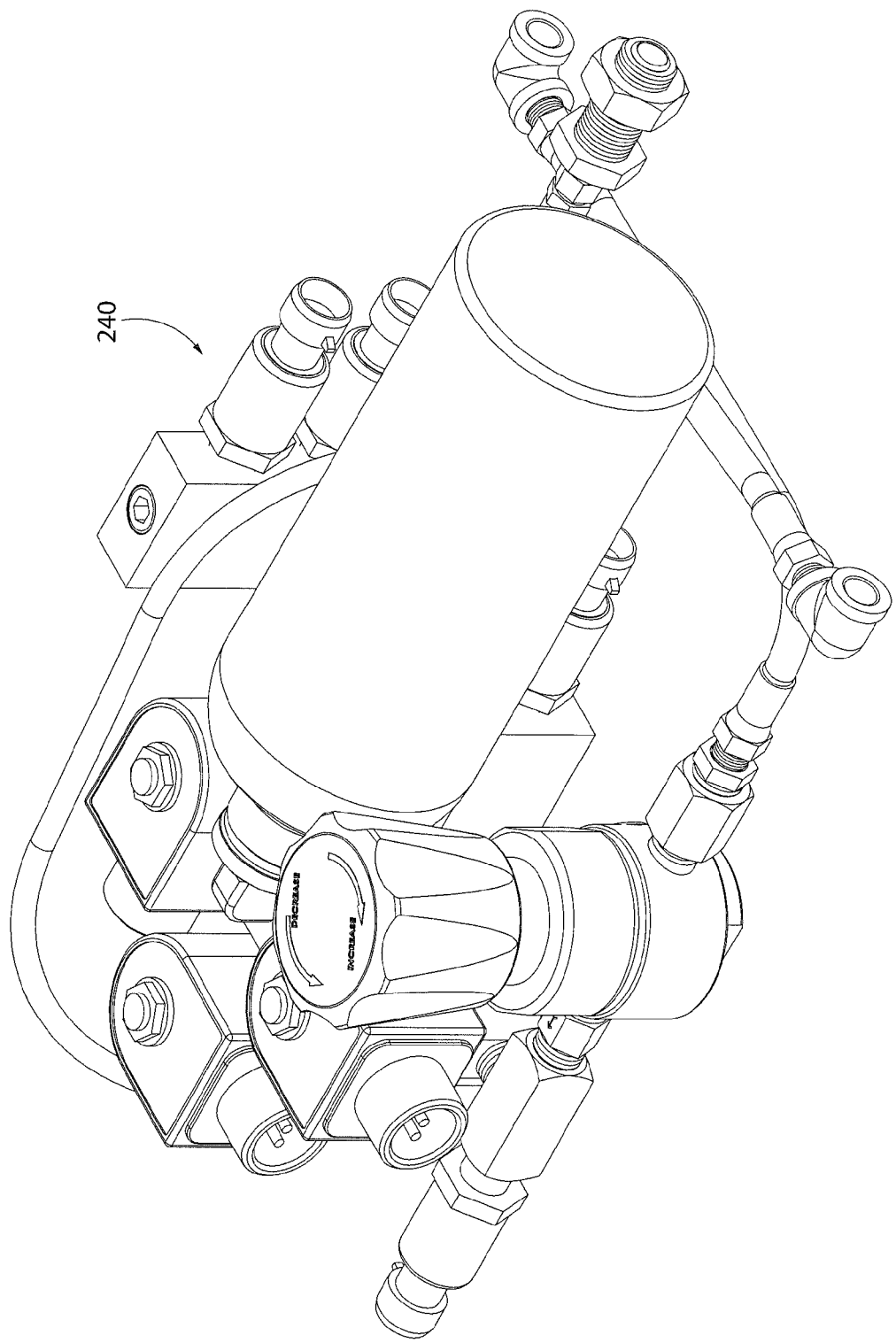

Turning to the drawings, FIG. 5 shows a complete and closed auto-fill fluid monitoring device 200 having case 202. Case 202 is constructed of top 210 and body 212. Case 202 can be a robust, sealable case having cut-outs for external interfaces such as ports or fasteners. In an embodiment case 202 connects top 210 and body 212 using a hinged connection with top 210 and body 212 sealing using a gasket therebetween when closed. In embodiments, case 202 is constructed predominantly of polymer but other materials including any material suitable for constructing a housing including but not limited to metal, natural materials, such as wood, other plastics or manufactured materials. Also visible in FIG. 5 are gas test port 218, temperature probe port 216, and exhaust port 217. FIGS. 6A to 8B show additional views of auto-fill fluid monitoring device 200 and sub-assemblies thereof.

Auto-fill assembly 240 provides the capability to increase gas quantities in a monitored enclosure by providing additional gas from fill bottle 262. Major components of auto-fill assembly 240 include manifold 242, solenoid valve 244, check valve 246, pressure regulator 248, filter assembly 250, transducer assembly 252, relief valve 254, exhaust assembly 256 first transducer 258, and second transducer 260. Other elements used in the construction of auto-fill assembly 240 include one or more of a restriction orifice, a pipe elbow, a pipe nipple, a pipe compression elbow, a pipe T-junction, a male to female or female to male converter, a port plug, a pipe reducing bushing, a hose, a portion of tubing, an adapter, and/or combinations, multiples, and variants thereof. Such elements as shown in, e.g., FIG. 6A, can be referred to herein as fluid connectors or fluid conduits. In an example embodiment, first and second transducers can be qualitatively distinct (e.g., first transducer 258 is a 100 PSI transducer, second transducer 260 is a 200 PSI transducer). In embodiments, one or more of the transducers can form a gas transducer assembly. Further, piping, tubing, and other elements can be of differing diameters throughout or beyond auto-fill assembly 240.

In auto-fill assembly 240 and elsewhere in auto-fill fluid monitoring device 200, various connectors or fasteners (e.g., screws, pins, nuts; bolts, lock rings), other hardware such as washers, springs, and shims, and/or fill bottles and associated hardware (e.g., connection adaptor, fill bottle cap) can be employed to finalize or reinforce the structure and organization of device 200.

Figure 7A:
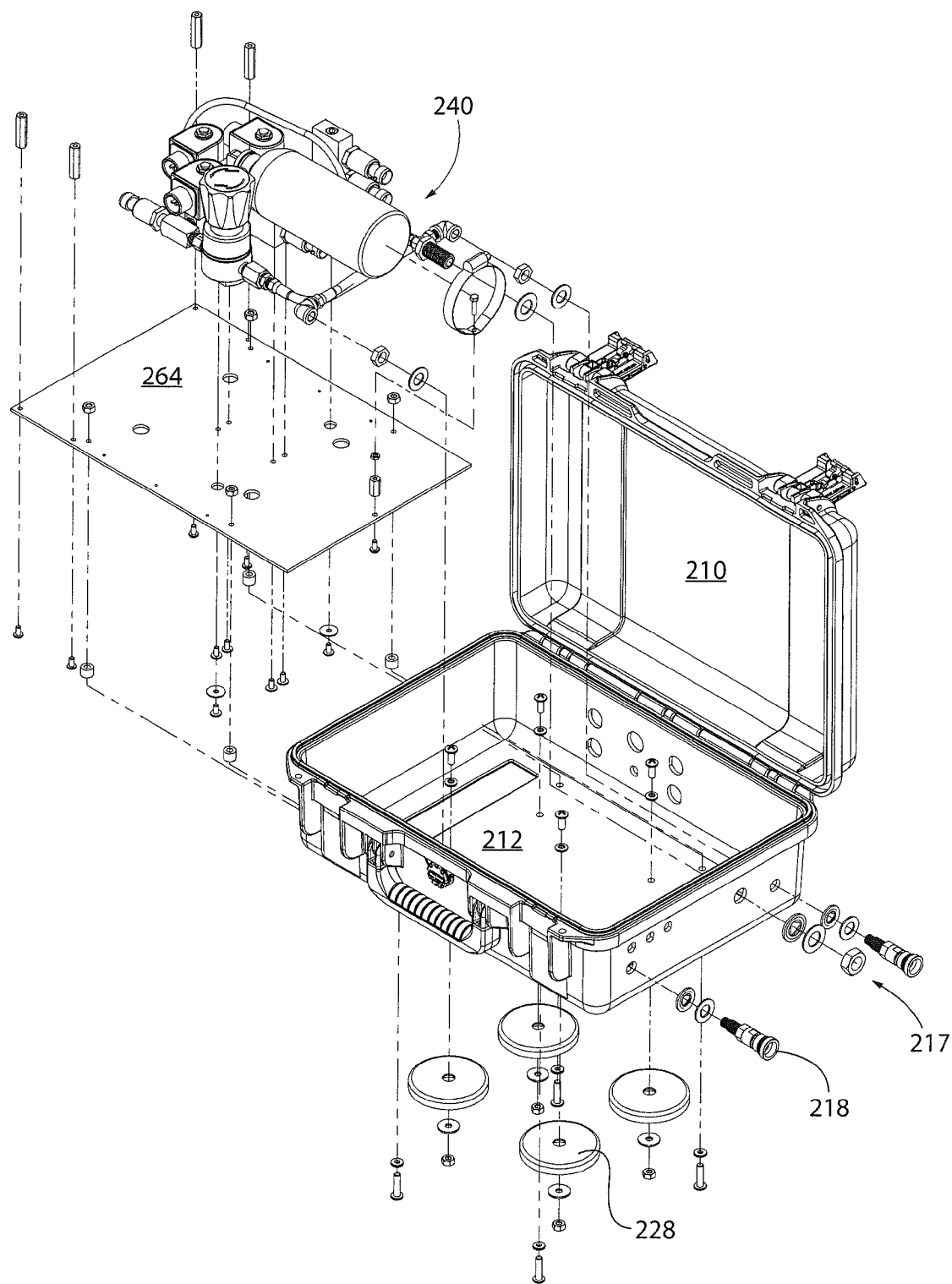
FIGS. 7A and 7B illustrate an example embodiment showing the integration of an auto-fill sub-assembly with a case for fluid measurement apparatuses.
Figure 7B:
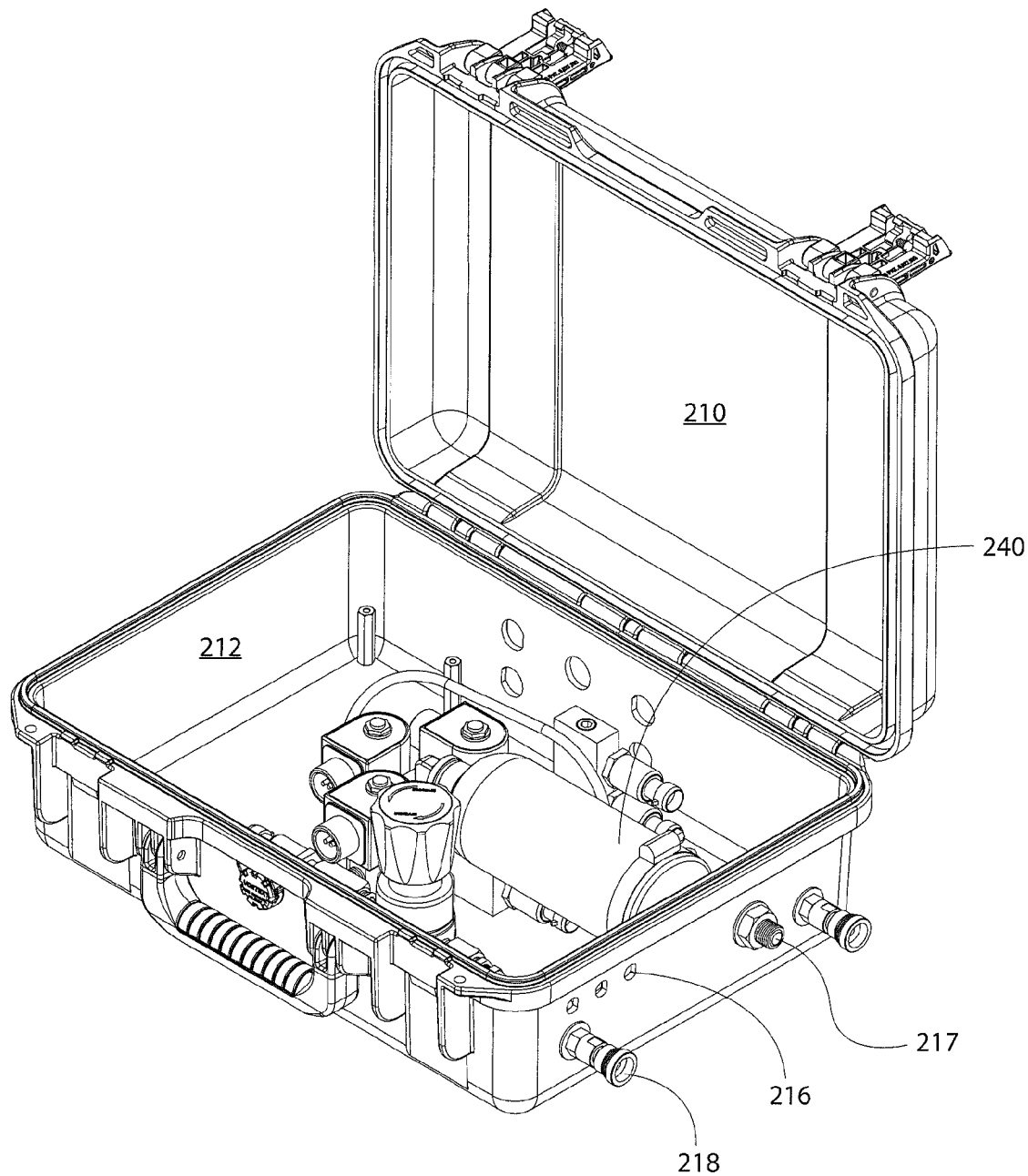

FIGS. 7A and 7B illustrate an example embodiment showing the integration of auto-fill assembly 240 into case 202 of auto-fill fluid monitoring device 200. Auto-fill assembly can be integrated into the case for the apparatus using base plate 264, various standoffs, spacers, risers, and/or washers, clamps, magnets, and other components. Further, as shown in, e.g., FIG. 7A, at least one magnet 228 can be attached to an opposing side of case body 212 using hardware passing through case body 212 and in embodiments base plate 264.

Figure 8A:
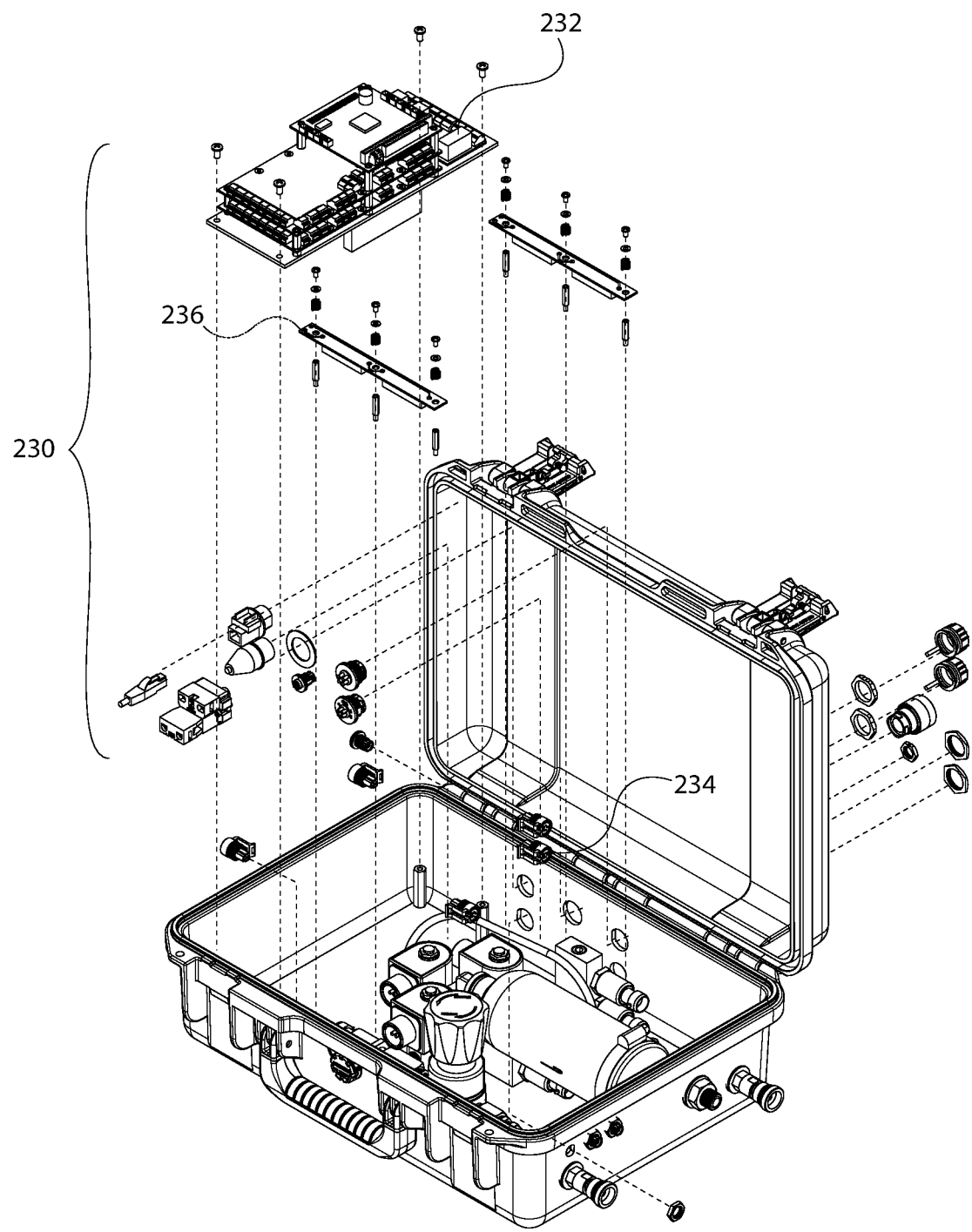
FIGS. 8A and 8B illustrate the integration of example fluid measurement sub-assemblies with a case containing an auto-fill sub-assembly.
Figure 8B:
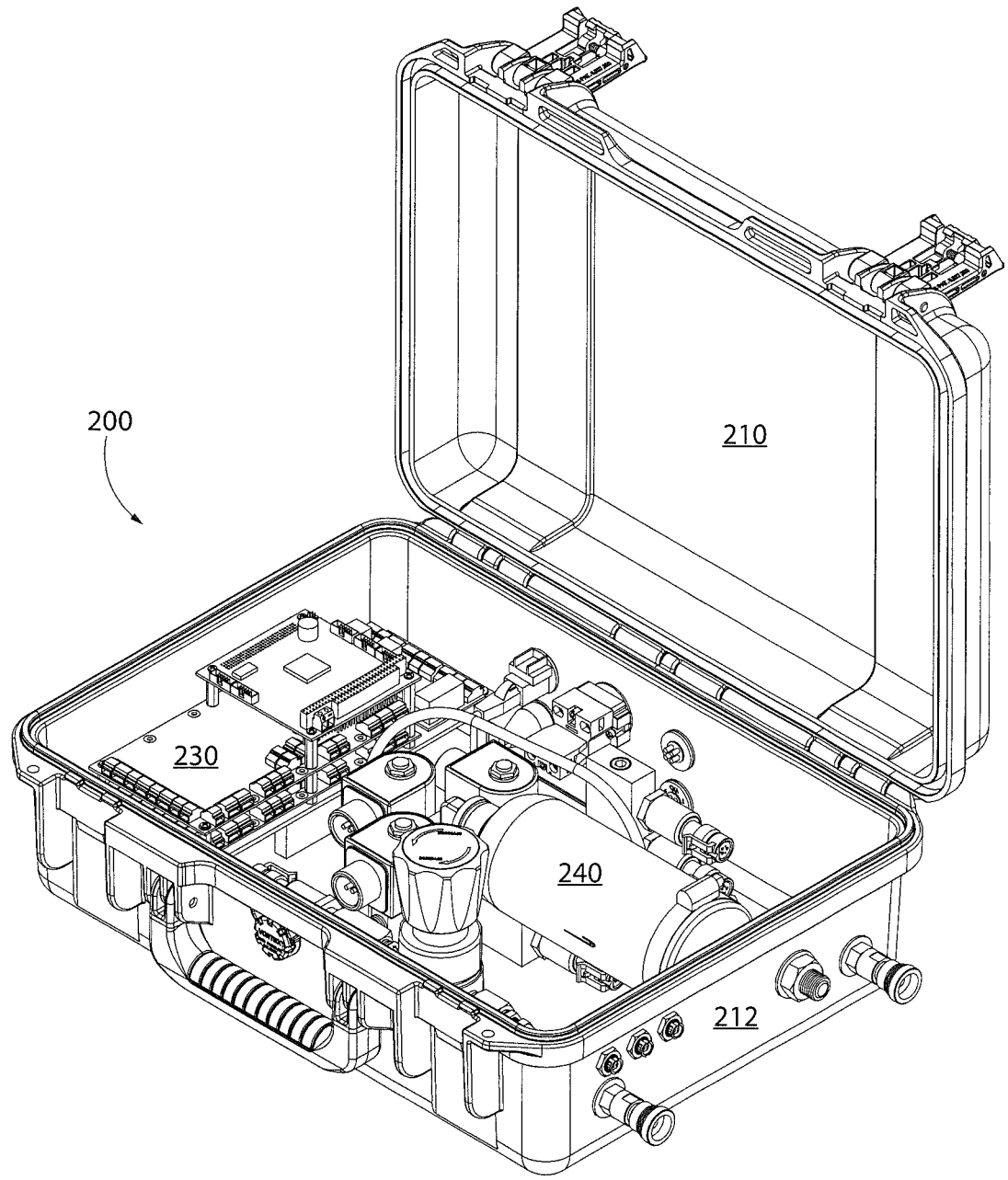

FIGS. 8A and 8B illustrate the integration the fluid monitoring assembly 230, including controller 232, into auto-fill fluid monitoring device 200. While multiple controllers may be provided, controller 232 can perform multiple functions and redundantly or independently subsume the various capabilities of different aspects described. Other components of fluid monitoring assembly 230 include transducer connector assembly 234, heater board 236, temperature probe port 216 and associated port assemblies, indicator-actuator 214 and associated electrical assemblies, power port 220 and associated electrical assemblies, network port 224 and connectors for enabling communication with controller 232, local data port 222 and connectors for enabling communication with controller 232, protective housings and covers for such ports, et cetera.

Figure 9A:
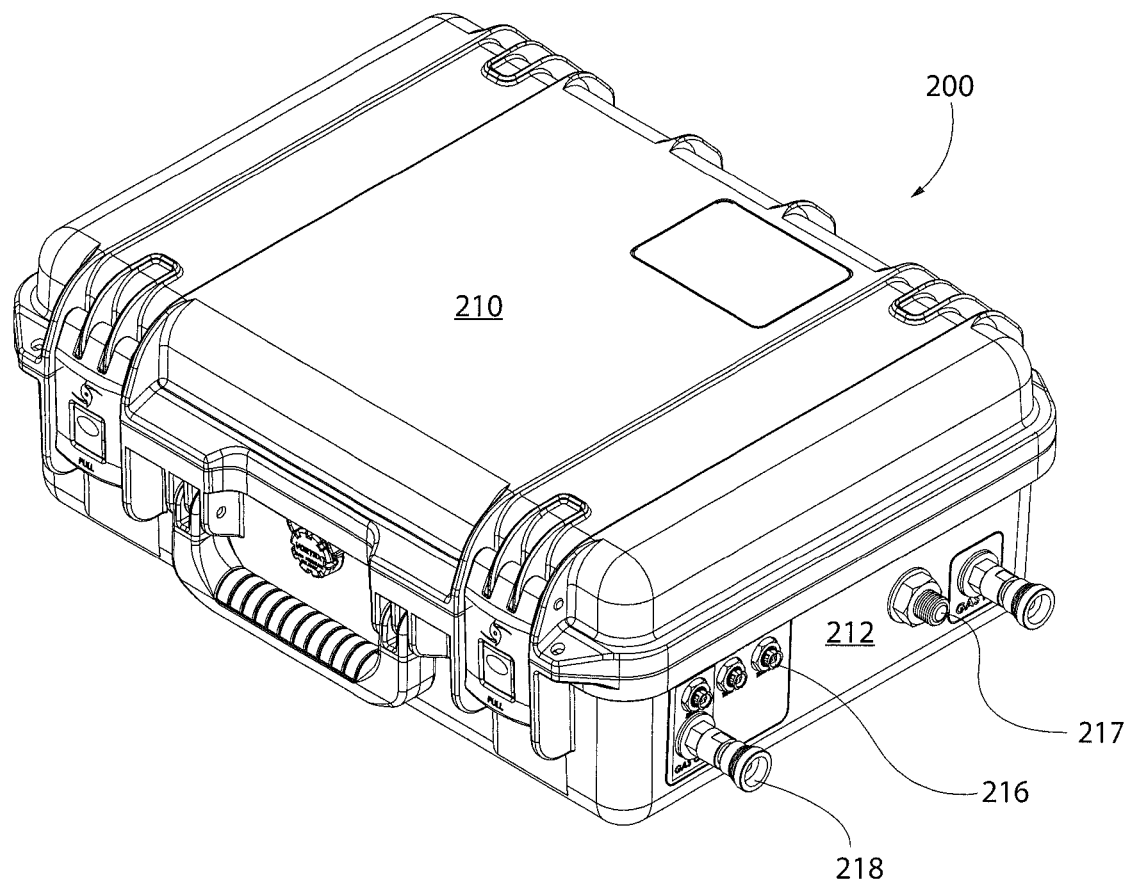
FIGS. 9A, 9B, and 9C illustrate alternative views of an example fluid measurement apparatus with auto-fill capability.
Figure 9B:
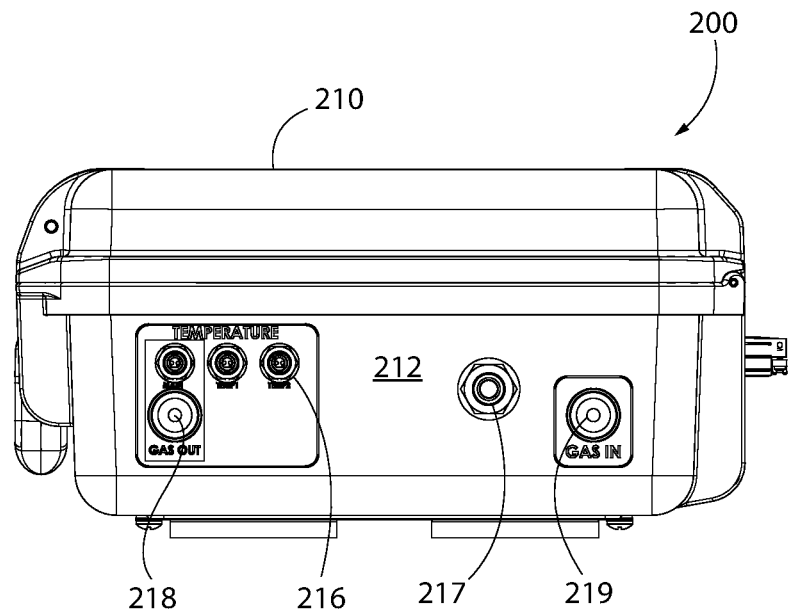
Figure 9C:
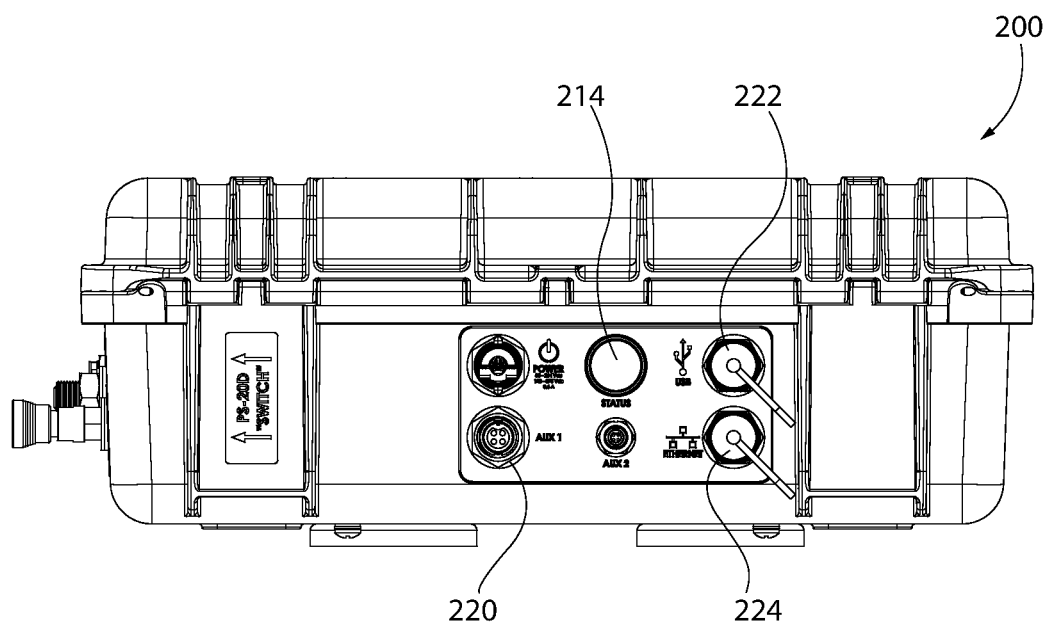

FIGS. 9A, 9B, and 9C illustrate alternative views of auto-fill fluid monitoring device 200. Case 202 including top 210 and body 212 are visible, as are the various ports and components establishing communication between the internal case elements and external structures with which they interact. Shown clearly are temperature probe port 216, gas test port 218, exhaust port 217, power port 220, indicator-actuator 214, network port 224, and local data port 222. A wireless port can also be integrated in or operatively coupled with controller 232 to permit wireless communication. Further, a gas fill port can be provided to recharge fill bottle 262 without opening or disassembling auto-fill fluid monitoring device 200.

Other aspects included in or related to auto-fill fluid monitoring device 200 can include a power cord assembly, one or more attachment hose assemblies, one or more temperature probe assemblies, fittings, electrical and electronic ports, data cables, a bushing and drill assembly, and various straps for retaining detachable pieces or the case itself.

Devices disclosed herein such as fluid monitoring devices 100 and 100', and auto-fill fluid monitoring device 200 provide sensor data related to a fluid enclosure and associated components. This data can be provided as-detected or transformed through processing into computed values and provided to one or more user interfaces. In embodiments, fluid monitoring devices or auto-fill fluid monitoring devices can have embedded user interfaces or feedback (e.g., different colors or lighting patterns for indicator-actuator, additional visual or audible elements included). In alternative or complementary embodiments, user interfaces are provided as displays on remote devices, to include desktop and notebook computers, tablets, phones, personal digital assistants, televisions, remote or local control systems, diagnostic equipment, et cetera, and receive at least data for display by wired or wireless connections to, e.g., a wireless port, network port, and/or local data port. The displays can be displayed to such devices through, e.g., a web browser, mobile application, computer program, or other means. The user interfaces can update in real-time or have a refresh rate slower than the rate at which data is monitored aboard the monitoring device and/or remote components assisting with processing.

Figure 10:
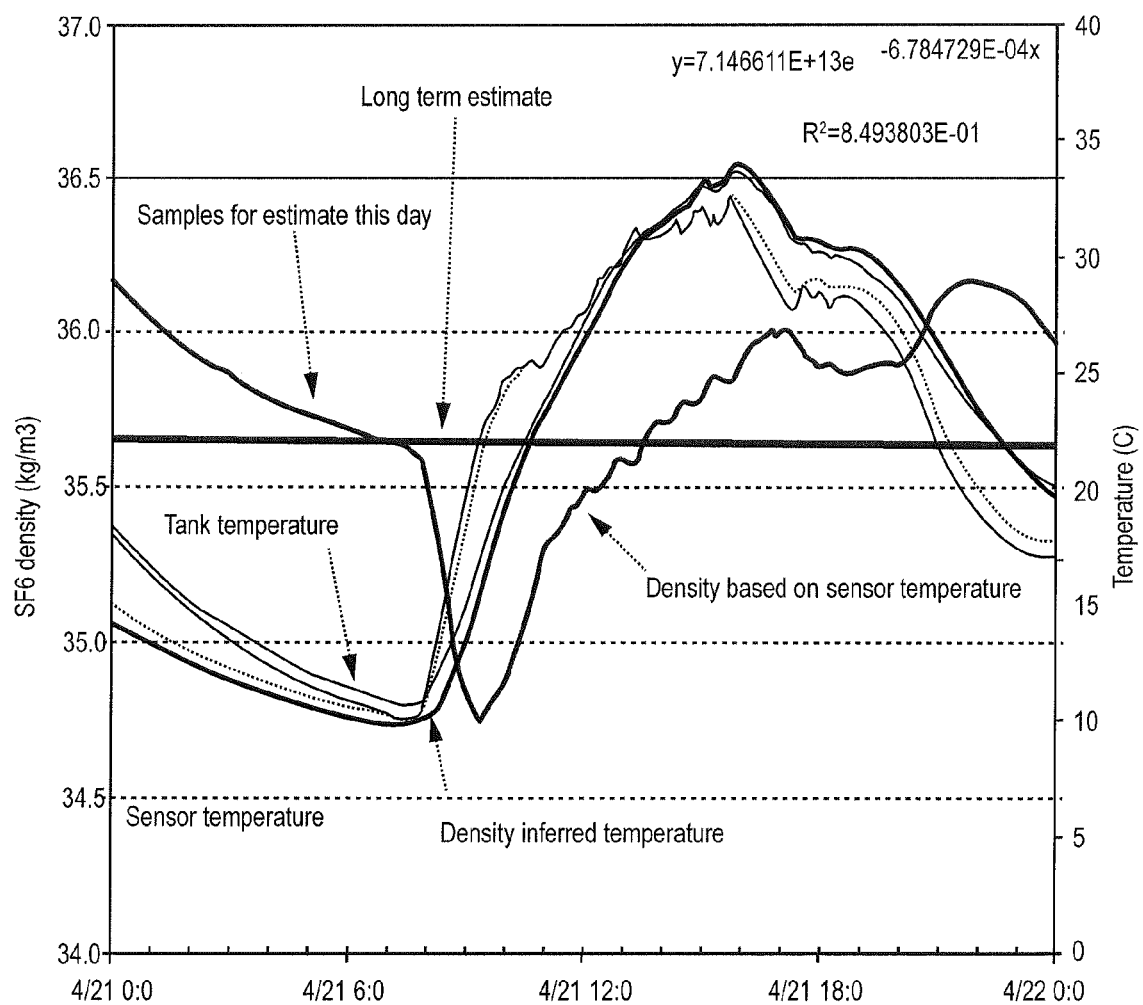
FIG. 10 illustrates an example graph depicting temperatures and densities associated with a gas enclosure under monitoring.

The measurements and processing performed using fluid monitoring devices are demonstrated at least in part by way of FIGS. 10-21, which show example data collected, calculated, and transformed using an embodiment of systems described herein at a testing location during an example time period of several months. FIG. 10 illustrates an example of discrepancies as a result of diurnal temperature variance, demonstrating the basis of some processing completed in accordance with disclosures herein. The X-axis illustrates time, while the Y-axis provides gas density or temperature. The graph illustrates how sensor temperature can depart from true tank (e.g., fluid enclosure) temperature, and how discrepancies are introduced to gas density estimates as a result. Individual or aggregate measurements can include further error as sensors and monitoring equipment can be installed to track averages in two or more fluid enclosures, or based on calculatory assumptions such as constant density in conjunction with measured pressure. While divergences are most visible, it is also noted that the curves converge during times of ambient temperature stability.

With this in mind, possible temperature discrepancies can be reduced in several manners. The positioning and use of one or more temperature probes can limit discrepancies. Positioning considerations can include shielding the probe from the heat sources such as sunlight (or surfaces absorbing substantial heat therefrom), heaters, vents, et cetera. Positioning of the sensor can also seek to observe the intended gas temperature rather than any ambient temperatures. In this regard, measuring portions the sensor can be enclosed in a manner isolating it from ambient influences. Additionally, sensors of low thermal mass will be most responsive to registering temperature changes.

Figure 11:
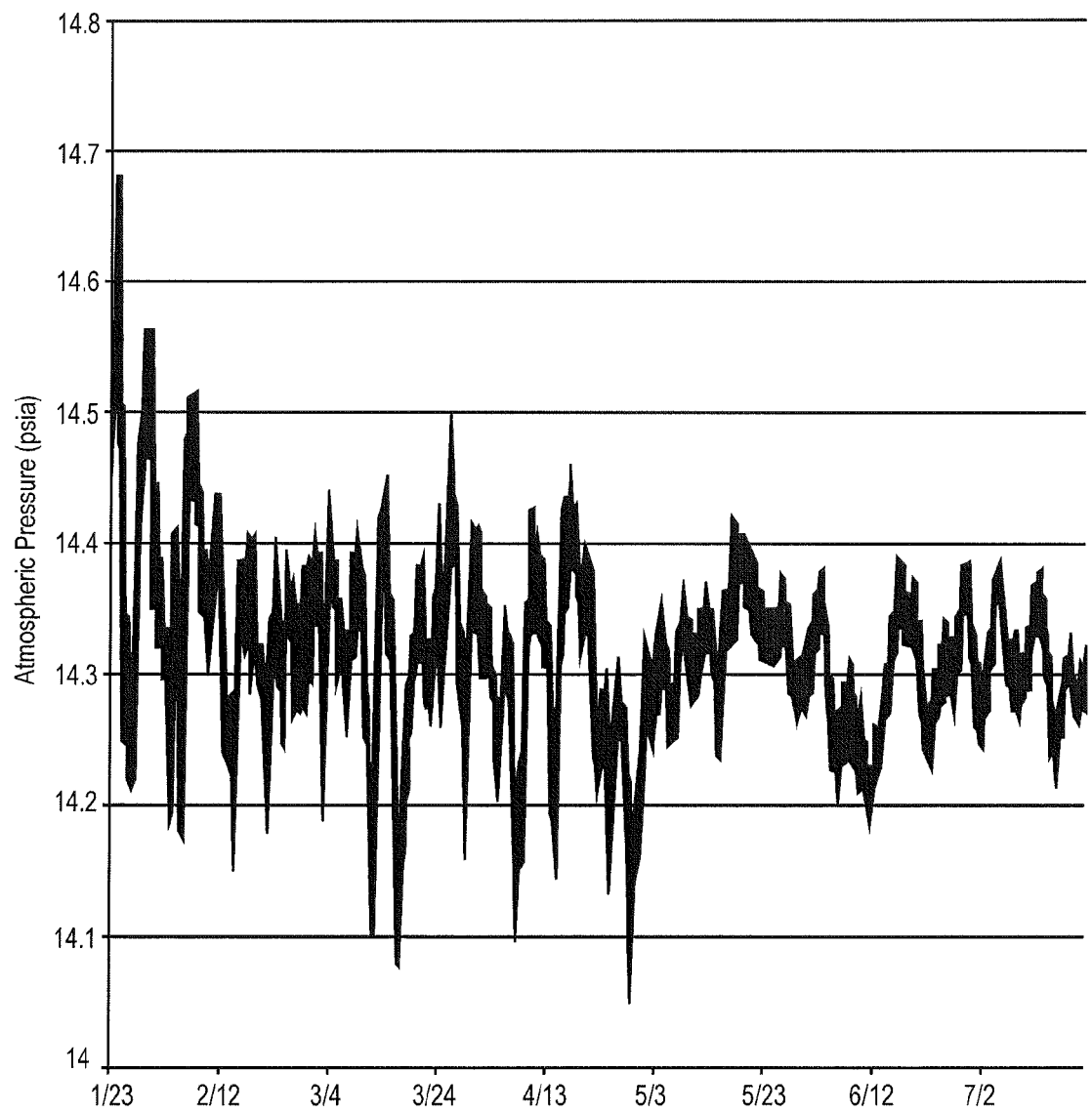
FIG. 11 illustrates an example graph depicting variations in pressure.

Besides temperature discrepancies, pressure inaccuracies can be reduced by use of an atmospheric pressure sensor to detect varying barometric pressure. FIG. 11 illustrates how atmospheric pressure can change over the course of days or weeks. Compensating for these uncontrollable changes will improve the accuracy and consistency of pressure measurements.

Discrepancies from temperature and pressure can not only cause reading errors, but can also trigger false alarms or lockouts. Safety systems (e.g., some circuit breakers) relying on gas density for a factor of safety (e.g., dielectric to prevent arcing within a circuit breaker) can sound an alarm or trigger a shutdown if the gas density is calculated outside the operating range. Because the rate of change of gas density may be very small, continued use may occur for long periods of time near the bounds of the operating range. As a result of such discrepancies, shutdown (e.g., lockout in a breaker) may occur unexpectedly well before an unsafe condition is present. In many applications, downtime and/or resuming operation can be expensive and present additional burdens. On the other hand, overpressure and similar issues present further problems which risk operational stability. Thus, sensors and other equipment can be configured to avoid discrepancies from temperature or pressure.

Signal processing can also be employed to improve accuracy and timeliness of feedback. Data from sensors can be processed to calculate, filter, and confirm gas density values. Signal processing can be used to determine or estimate gas density values under static (e.g., relatively constant) or dynamic (e.g., slow leak, fast leak, gas fill, gas removal) conditions. Signal processing can also provide or improve confidence in related or independent gas density values, track trends in gas density levels, estimate future gas density levels (e.g., in units and/or with reference to threshold levels), estimate gas loss over periods of time, log gas fills (or removals), transmit and display measured and calculated/derivative values (e.g., to show pressure gauge or thermometer values which can be used to track expected response in mechanical components such as switches, to show variance throughout system, to show error levels), capture and analyze high-frequency vibrational information (from, e.g., breaker operation, compressor operation, weather conditions, technician or other movement or work), and prepare and communicate reports based on these and other values or activity.

While these and other portions discuss signal processing, collected data can be saved into a pre-processed log which is not overwritten to permit reference to the "raw" data for inspection or re-processing.

While not required, signal processing techniques can be segregated by timeframe, with such categories including high frequency, real time, short term, mid-term, diurnal, long-term, and historical.

High frequency processing can be used to, e.g., capture and analyze high-frequency vibrational information from, e.g., breaker operation, compressor operation, weather conditions, technician or other movement or work.

Real time processing can be used to measure variables for which high granularity data is required to monitor gas density or other values. These variables include, but are not limited to, and may not in all embodiments require: switch internal temperature signal; a primary lever signal (e.g., by reflective object sensor); a secondary level signal (e.g., by Hall effect sensor); atmospheric pressure signal; switch contact voltage signals; external temperature signal(s) (e.g., one or more); and system variables (including, but not limited to, e.g., reference voltages). These signals can be processed to produce calibrated measurements for the sample period. The calibrated measurements can include, but do not require all of, and are likewise not limited to: $T_S$ sensor temperature in degrees Celsius; $P_{GAS}$ gas pressure in pounds per square inch gauge; $P_{ATM}$ atmospheric pressure in pound square inch absolute; $S_{STATE}$ switch contact state as open or closed; $V_{SO}$ switch open voltage (based on, e.g., control voltage sensed during open contact state); $V_{SC}$ switch closed voltage (which can be calibrated to, e.g., avoid contact degradation or over-current condition); and $T_{EXT}$ external temperature in degrees Celsius.

Using measured and calculated values, equations and algorithms can be employed to determine a real time density estimate. In an embodiment, a second order virial equation for estimating gas density includes:

$$P = R \cdot T \cdot \left( \frac{n}{V} + B(T) \cdot \frac{n^2}{V^2} \right)$$

Where $d_{RT}(t)=n/V$ is the gas density, $P=P_{GAS}+P_{ATM}$, $T=T_S+273.15$ (absolute temperature), R is the gas constant, and $B(T)$ is the temperature dependent second order virial coefficient for the particular gas (e.g., SF6 in breaker).

The density estimate can additionally be used in other calculations, such as computation of a temperature corrected pressure. In an example, a temperature corrected pressure $P_{20}$ can provide a temperature corrected pressure corresponding to the gauge pressure at a reference temperature of 20 degrees Celsius. Other reference temperatures can be utilized as well.

$P_{GAS}(t)$ can also be used to detect high speed events such as breaker operation, compressor operation, and vibration events.

Errors in $d_{RT}(t)$ relative to actual gas density $d(t)$ can arise from factors such as measurement errors (in, e.g., $T_S$, $P_{GAS}$, and $P_{ATM}$) and other discrepancies (e.g., difference between $T_S$ and the effective gas temperature $T_{GAS}$).

In embodiments, real time can include processes executed in one second or less. In embodiments, other timeframes for real time or short term (or an intermediate term) can be realized to ensure processing availability in all timeframes.

With respect to short term processing, real time series can be passed through a low-pass filter mechanism to yield short term series (e.g., of gas density over time). By filtering the real time calculations, short-term noise attributable to measurement variations can be disregarded while still detecting significant steps in gas density on a short term timeframe such as gas fill (or re-fill) and/or significant gas loss from maintenance activity or large leak (e.g., failure of one or more seals, failure of vessel wall, unintended opening of vessel).

Density steps can be detected resolving a difference between density measurements at different times. In an embodiment, the difference can be resolved using the equation:

$$\Delta d_{ST}(t) = d_{ST}(t) - d_{ST}(t - N^*\tau)$$

Figure 12:
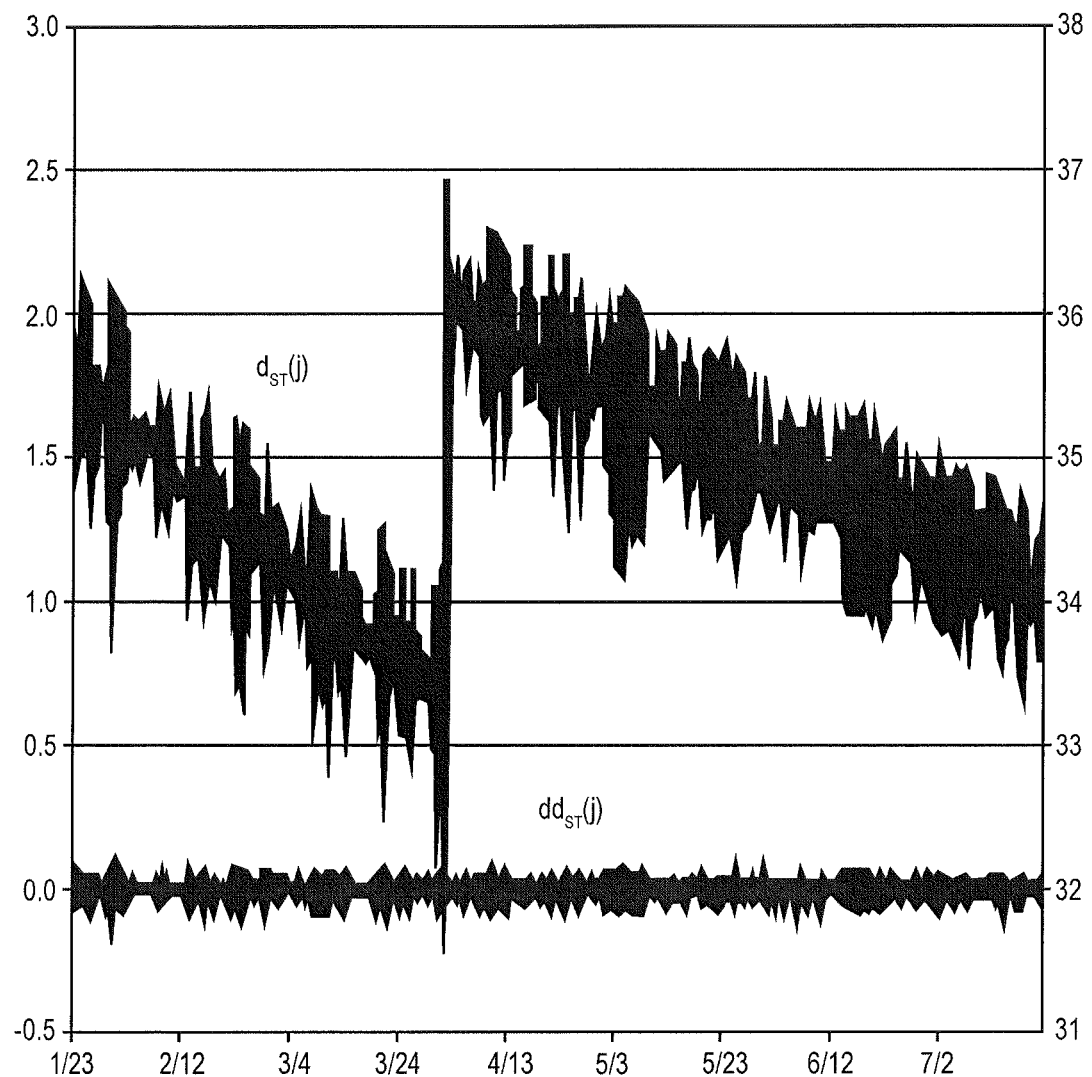
FIG. 12 illustrates an example graph depicting short term gas density in a gas enclosure.
Figure 13:
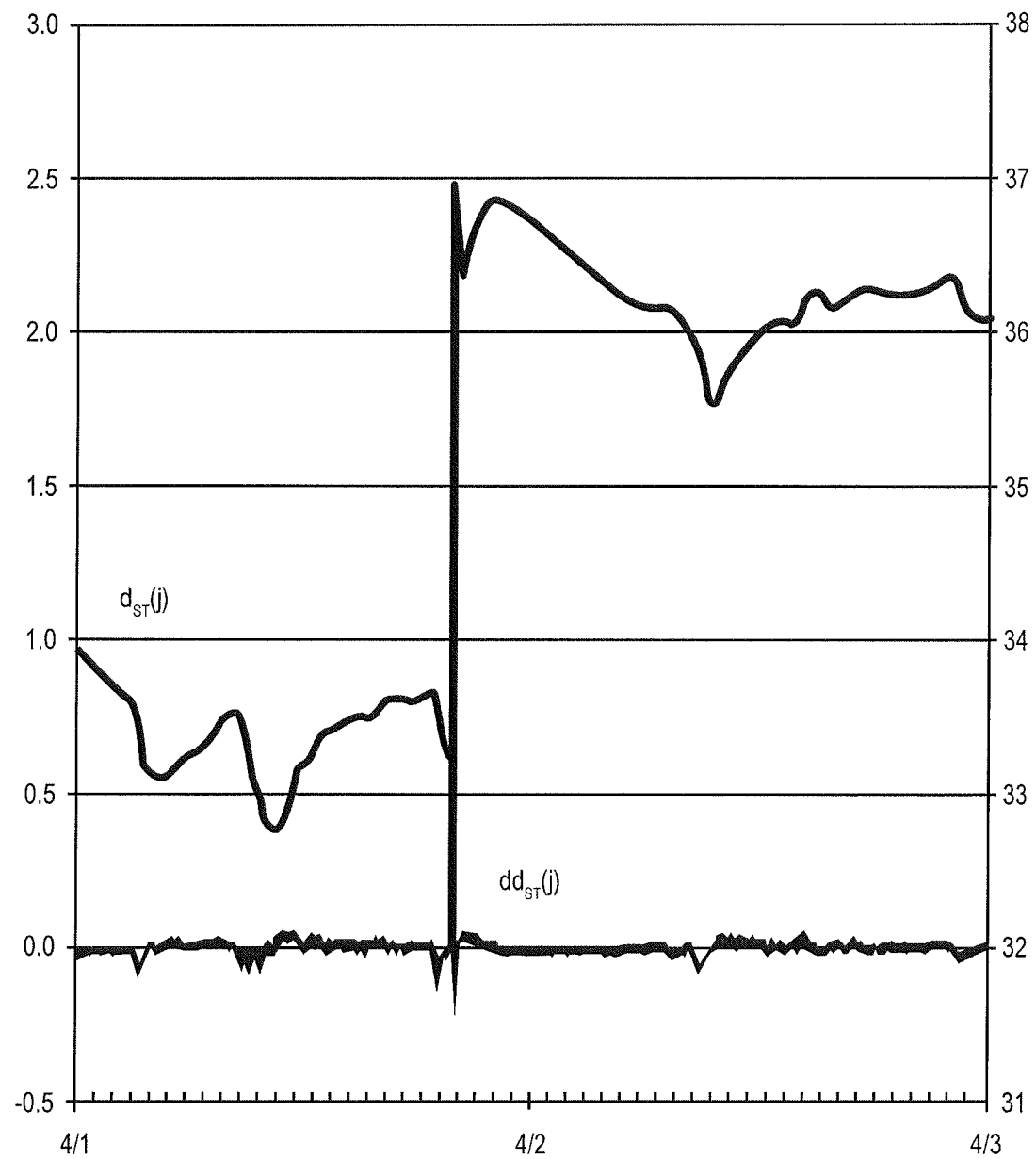
FIG. 13 illustrates an example graph depicting short term gas density in a gas enclosure at higher resolution than FIG. 12.

FIG. 12 shows $\Delta d_{ST}(j)$ for a test period of a breaker, where N=300 and $\tau$=1 second, implying a 5-minute resolution in data points. FIG. 13 shows a closer view of a breaker fill event and provides a more detailed view of density measurements occurring over a shorter history.

In embodiments, density processing can be contingent upon the detection or inference of a density step. In one such embodiment, such a density step can be inferred based on $\Delta d_{ST}(t)$ exceeding a threshold. Additional processing can assist with the detection of significant short-term density changes. In at least one embodiment, the value of $d_{ST}(t)$ can be compared to a current long term density estimate, $d_{LT}(t)$. When the absolute value of the difference between the short term value and long term estimate exceeds a threshold, a density step can be inferred and density processing invoked. In an alternative or complementary embodiment, a day-to-day difference in the long term density estimate can be compared to a representative diurnal density estimate, $d_{DR}(t)$, assessed following the flattest temperature region (where t is $t_{BEST}$, described infra). When the comparison determines a difference between $d_{DR}(t_{BEST})$ and $d_{LT}(t_{BEST})$ exceeding a threshold, a density step is inferred and density processing invoked.

Figure 14:
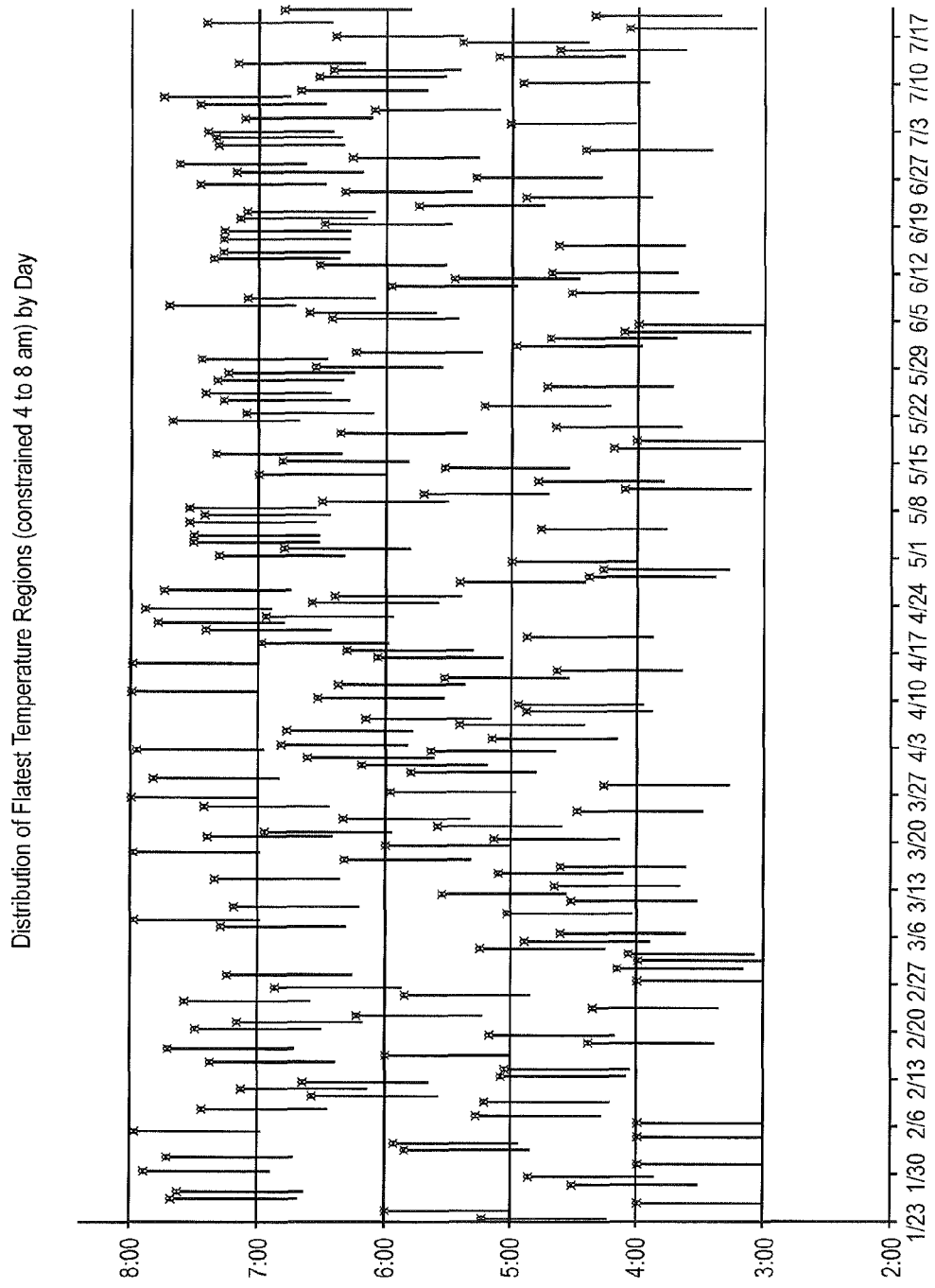
FIG. 14 illustrates an example plotting of daily temperature windows and selected sample times relating to temperature stability.
Figure 15:
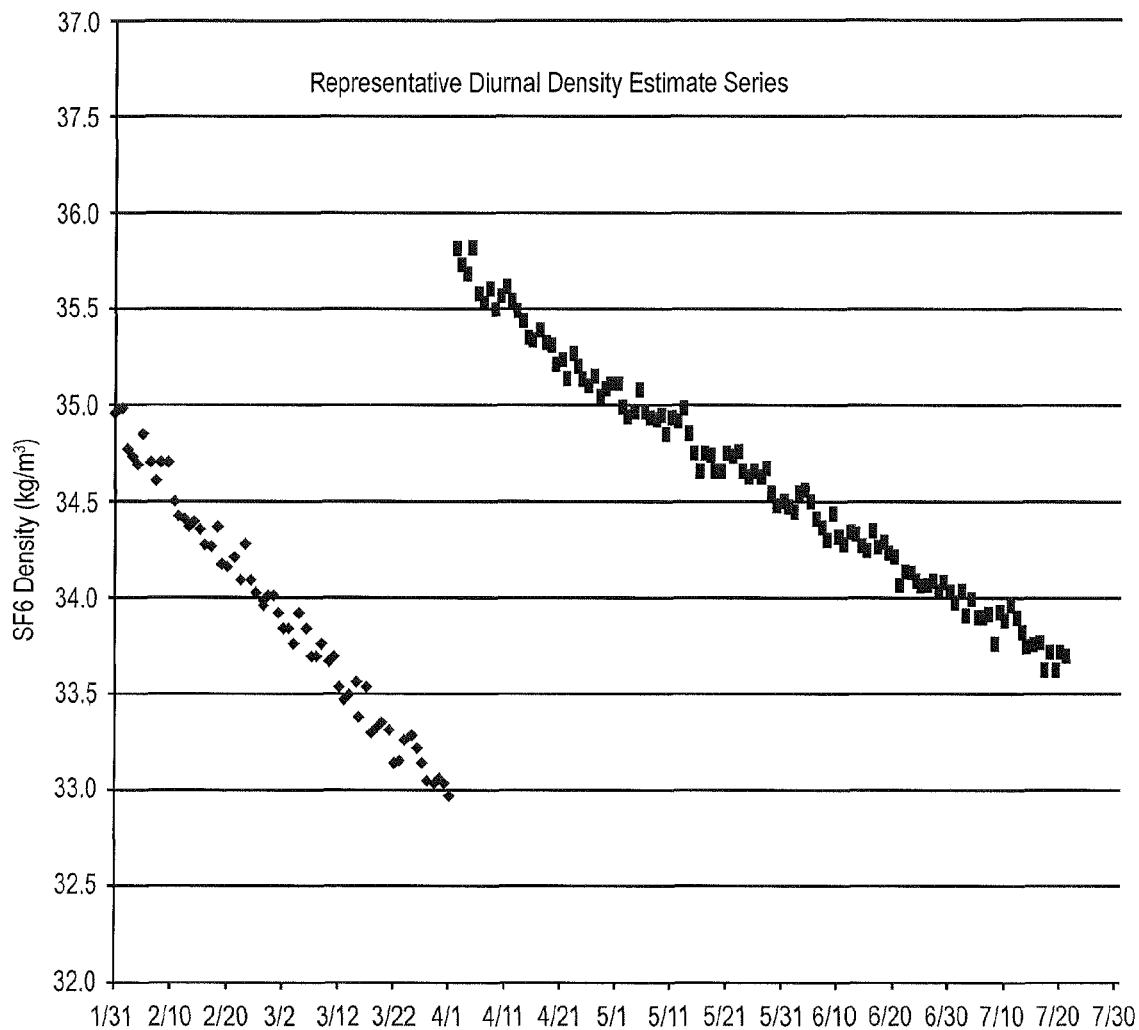
FIG. 15 illustrates example plottings of representative diurnal density estimate series.
Figure 16:
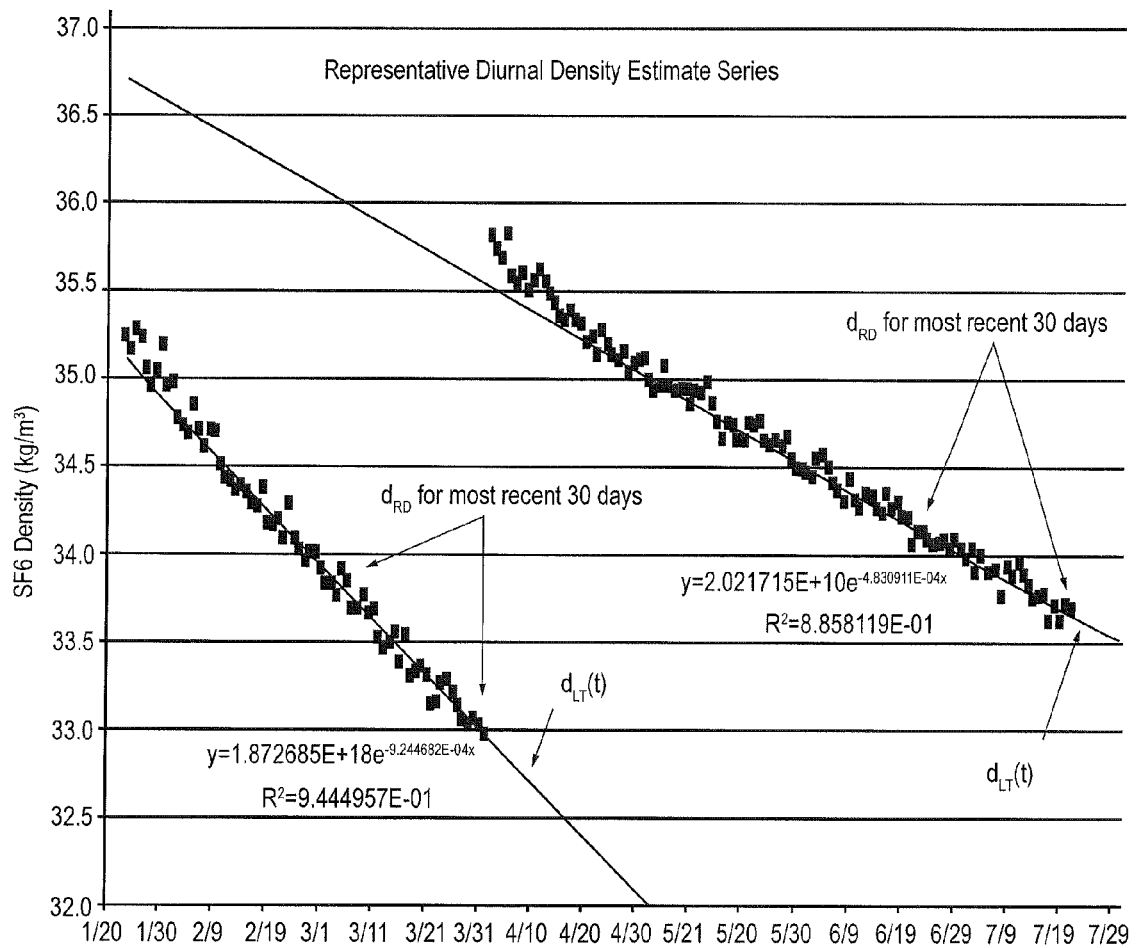
FIG. 16 illustrates example trend lines predicting representative diurnal density estimate series.

Diurnal processing can be used during periods of slow gas density change, such as in the presence of a slow leak, to establish a daily density time series. This daily density time series can be based on a period of each day having the least variation in sensor temperature $T_S$, which can provide a close relationship between $T_S$ and $T_{GAS}$. Various programmable parameters can be employed for diurnal processing, including: $H_{BS}$, the hour of the day to begin seeking the least-variable ("flattest") temperature region; $H_{ES}$, the hour to stop seeking the flattest temperature region; $\Delta t_{RSMIN}$, the minimum length of time to select; and $\Delta t_{SS}$, the sample size in time to process selected at the end of the flattest region found. $T_S(t)$ is examined over a variable period matched to the length of $\Delta t_{RSMIN}$ which initially begins at $t=H_{BS}$. $T_S(t)$ shifts along the timeline at a real time rate (e.g., samples of one second, samples less than one second) until $t=H_{ES}$. As each sample period is processed, a derivative value of $T_S(t)$ (e.g., the root mean square) for each period is calculated, and the period having the minimum derivative value (e.g., lowest root mean square) is identified. When a new minimum derivative value is identified, the period length is extended from the time of the new minimum while the derivative value remains less than or equal to the new minimum derivative value. When the beginning of next period coincides with $H_{ES}$, one or more periods having the minimum derivative value of $T_S(t)$ of size $\Delta t_{RSMIN}$ or larger is known. A sample of length $\Delta t_{SS}$ can be selected from the most recent portion of the minimum derivative value window at, e.g., time $t_{BEST}$ to represent estimated gas density based on $T_S$ at the time of day when $T_S$ may closely match $T_{GAS}$. This is illustrated in FIG. 14, which shows a series of selected sample times for a group of days, illustrating the distribution of "flattest" temperature region for each day in the group. This "flattest" temperature region can be referred to as a least variable temperature period.

Because $\Delta t_{SS}$ represents a small amount of time, and expected density changes in each period are expected to be small, the values of $P_{GAS}$, $P_{ATM}$, and $T_S$ can be averaged over the interval(s) to provide a representative gas density, $d_{RD}$, at the time of the sample for the respective day $t_{BEST}$. Diurnal processing accordingly creates a new daily density sequence of sample time data pairs [$d_{RD}$(day), $t_{BEST}$(day)], the representative diurnal density estimate series, which can be displayed as in FIG. 15 or utilized subsequently for long-term processing.

Long-term processing can be used, in embodiments, to compensate for errors in real-time density estimates $d_{RT}(t)$ relative to actual gas density $d(t)$, caused by, e.g., measurement errors in $T_S$, $P_{GAS}$, and $P_{ATM}$, and deviations between $T_S$ and $T_{GAS}$. Long term processing can employ, in embodiments, representative diurnal density series, one or more conceptual models of gas leakage, and curve fitting algorithms.

In embodiments, regression analysis can be utilized. In an embodiment, when representative density points $d_{RD}$(day) are available for three or more consecutive days, a regression analysis can be performed. Different regression models and the number of samples over which to computer the regression function can be selected in one or more embodiments. In an embodiment, an exponential regression can be used to estimate a long term density estimate:

$$d_{LT}(t) = b \cdot e^{(a \cdot t)}$$

where a and b are calculated to minimize the squared error:

$$\text{ERROR}^2 = \sum_N (d_{RD}(t_i) - d_{LT}(t_i))^2$$

The exponential regression can assist with modeling real world leaks where the rate tends to decrease with decreasing pressure (e.g., as where gas escapes from a fixed volume at constant temperature through a leak port of fixed resistance to gas flow, the rate of escape varies according to the pressure difference). However, leaks may evolve over time or have less predictable rates based on, e.g., variations in gas viscosity (e.g., higher temperatures increase gas viscosity decreasing leak rate). Limiting the number of data points included in a long term density estimate regression can assist with accounting for such variance. In an example, regressions can process samples from the previous 30 days, rather than longer historical data available. Such constraints balance error rejection due to, e.g., temperature disparities and larger samples spanning periods during which leak rates change (e.g., decline) at a rate (e.g., faster) than less-constrained exponential models typically predict. This is visible in the example provided by FIG. 16 which shows a decreasing slope in the curve illustrating $d_{LT}(t)$ as the leak rate slows. At various data points, the long term density estimate $d_{LT}(t)$ is defined by the value of the applicable best-fit function evaluated at time t.

Figure 17:
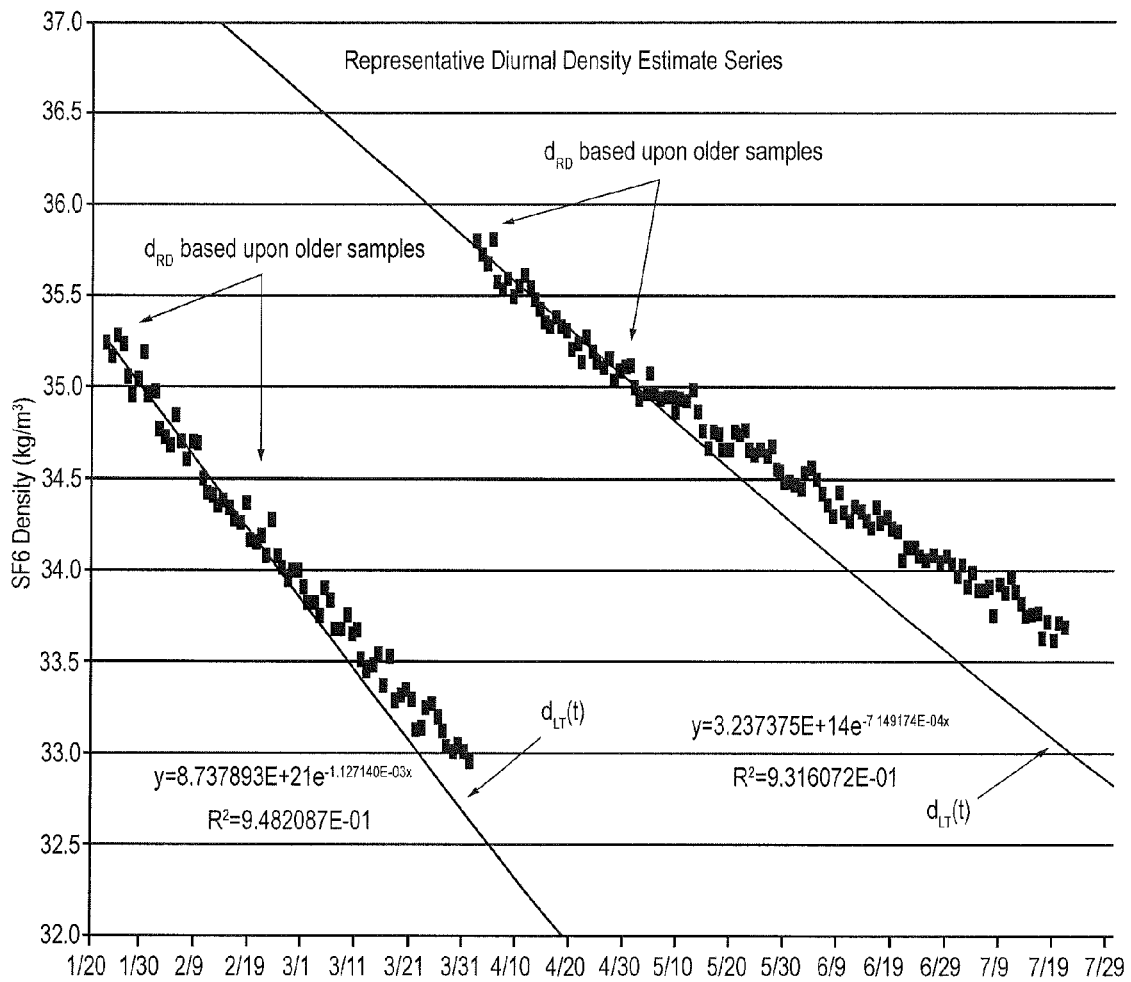
FIG. 17 illustrates example diurnal density estimate series and the changing gas leak rates of the gas enclosure related thereto.

FIG. 17 provides an example illustrated how leak rates decline at rates different than predicted by the exponential model. As described above, during each day a region of least temperature variation is identified and used to calculate a representative diurnal density estimate seeking to minimize error attributable to the difference between sensor temperature and actual gas temperature. As each point is added to the representative diurnal density estimate series, an exponential regression analysis can be performed on data points including the newly added point and a number of preceding points determined by parameter setting (e.g., 30 points inclusive, other numbers). The regression analysis yields two coefficients that determine a best fit (by, e.g., least squared error) exponential function over the data. This process produces two new series, $a_n$ and $b_n$, where n is an index representing the current day, and a and b are the coefficients of the most recent regression analysis completed when the representative diurnal density estimate for day n becomes available. This can more generally be characterized as a diurnal fill gas density with respect to the gas filling a fluid enclosure. In embodiments, using these series a most recent long term density estimator can be realized by the equation:

$$d_{LT}(t) = b_n \cdot e^{(a_n \cdot t)}$$

The most recent long term density estimation can be used to estimate the current density by evaluating the exponential equation with coefficients $a_n$ and $b_n$ for the current time t. The current density estimate can be reported to a user (e.g., using an interface). A coefficient of determination (the "$R^2$ value") can be reported in conjunction as a density estimate confidence. The $R^2$ value is a function of, e.g., the number of points in the analysis (more leading to greater confidence) and the degree to which the exponential estimator function matches the actual representative diurnal density points.

Further, where density thresholds or values of interest exist (e.g., density for alarm, density for lockout, density for overpressure), the exponential estimator can be employed to determine the time at which such density is expected to occur. In an example, a lockout time can be predicted using:

$$t_{lockout} = \frac{\ln\left(\frac{d_{lockout}}{a_n}\right)}{b_n}$$

Figure 18:
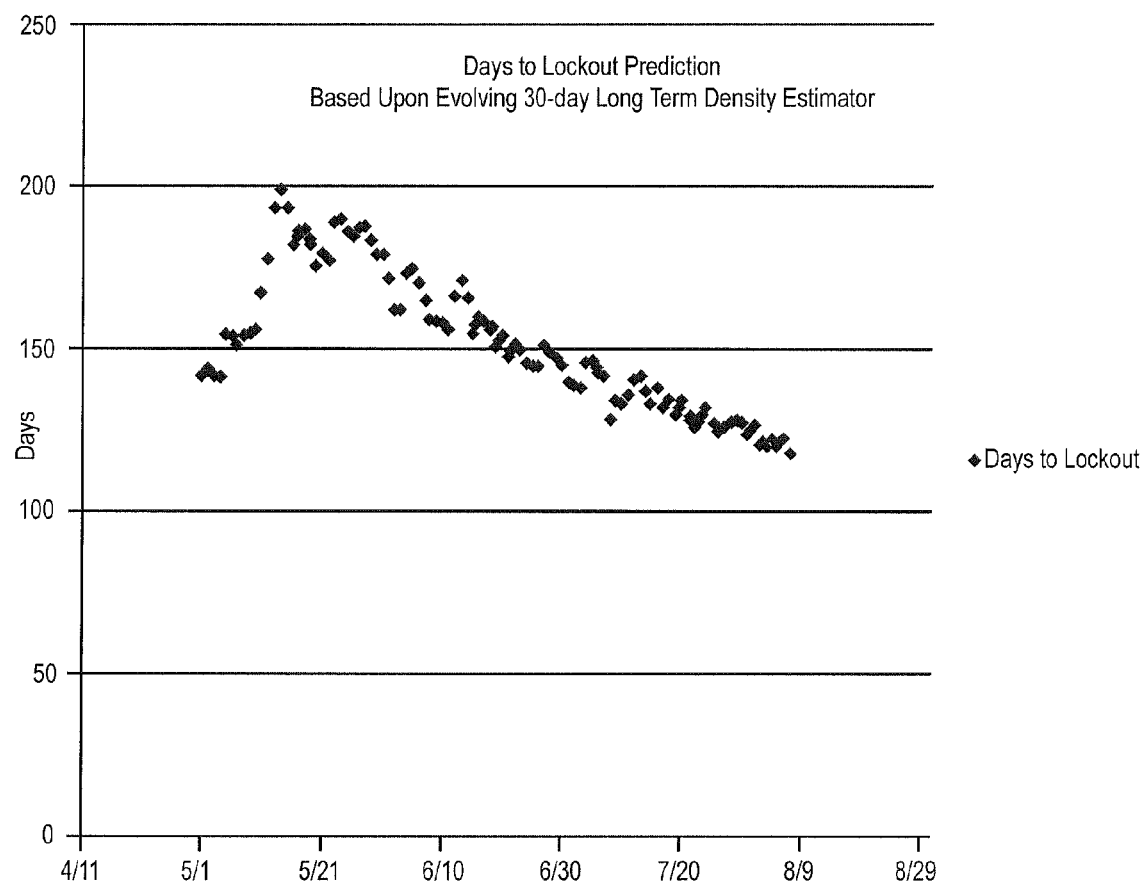
FIG. 18 illustrates an example plotting of days to lockout based on long term gas density estimates.

Using this equation along with the current long term density estimator, embodiments herein can track the time of lockout or time until lockout. FIG. 18 shows an example days to lockout predictor based on 30 day long term density estimates. More generally, these predictions, or those generated using regression models herein, can be referred to as estimated future fill gas density.

Figure 19:
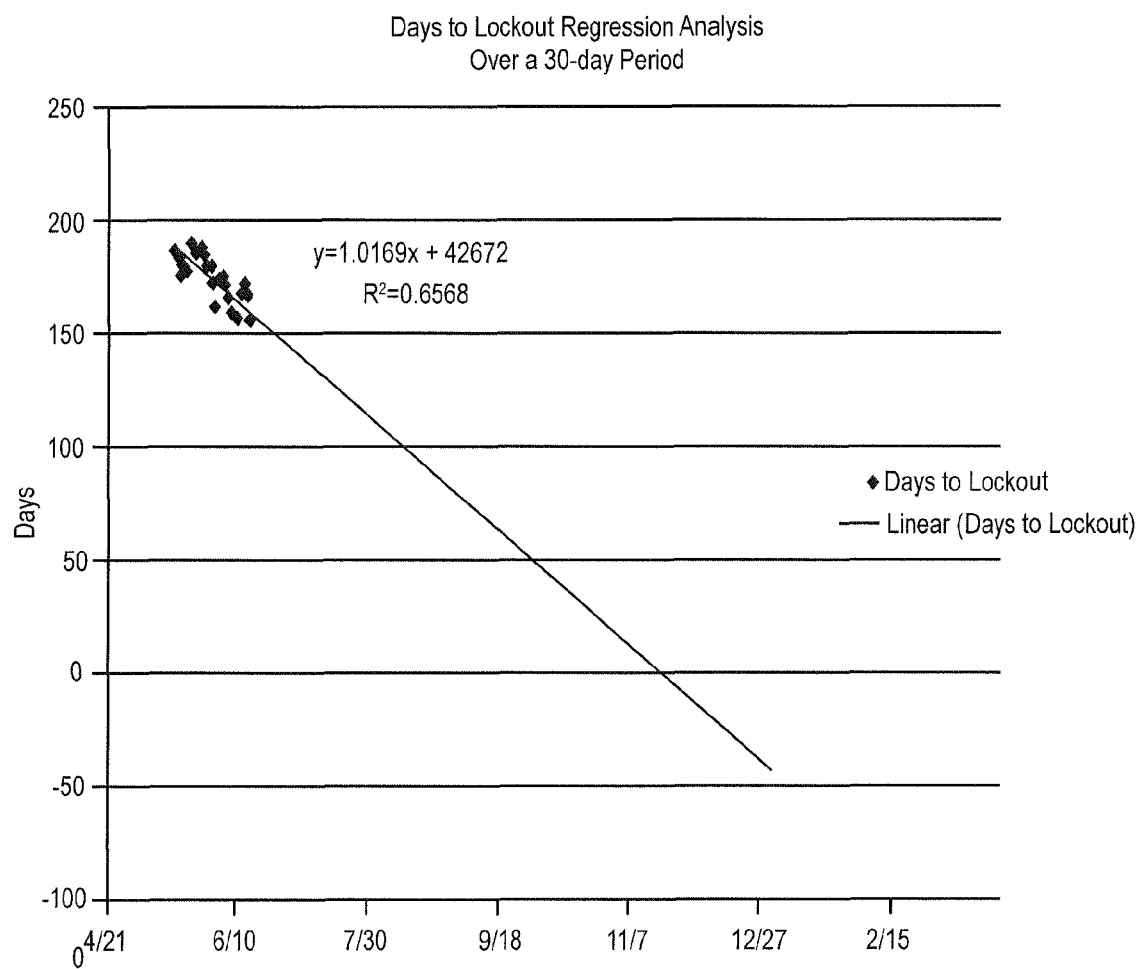
FIG. 19 illustrates an example lockout prediction based on regression analysis of gas density estimates.
Figure 20:
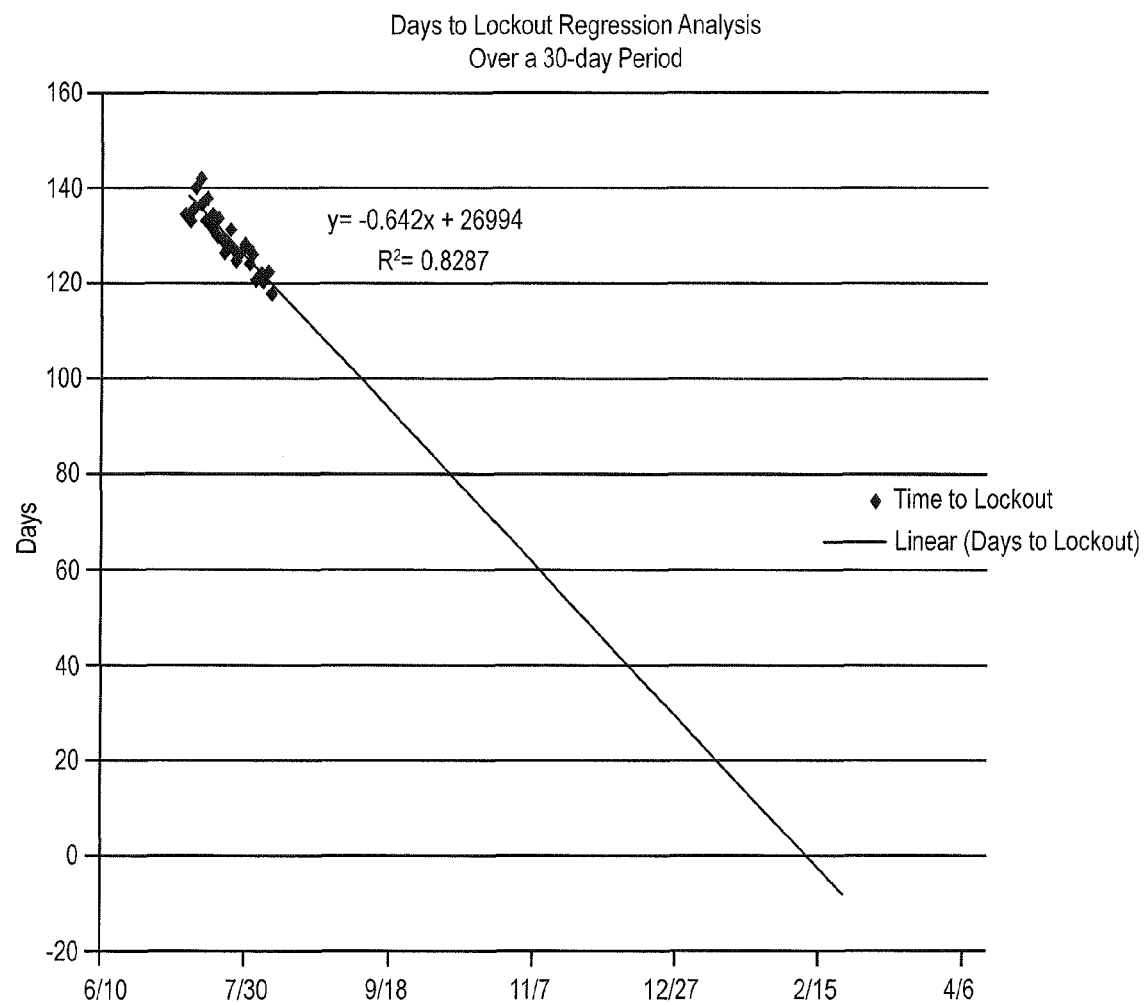
FIG. 20 illustrates another example lockout prediction based on web browser, mobile application, computer program session analysis of gas density estimates showing a slowing leak rate.

Deceleration (or, in alternatives, acceleration) in leak rate can also be modeled using regression analysis and low pass filtering. FIG. 19 depicts a linear regression analysis computed over 30 days of time-to-threshold estimates soon after the density settled following a refill of the gas. FIG. 20 illustrates how the projections change with time, as indicated by the example dates and values depicted. In the examples provided and in various embodiments, the linear regression is "well behaved" inasmuch as the data converges to zero on occurrence of the predicted event and the prediction becomes increasingly accurate as the time to the predicted event diminishes. Such techniques can be combined with additional filtering or other processing in embodiments.

Relatively abrupt density changes can also be predicted through analysis of data available to embodiments of systems and methods described herein. In an embodiment, a difference of short term density series can be detected using the equation:

$$|dd_{ST}(t)| = |d_{ST}(t) - d_{ST}(t - N^* \tau)| > THRESHOLD_1$$

The value of $d_{ST}(t)$ is compared to the current long term density estimate $d_{LT}(t)$:

$$|d_{ST}(t) - d_{LT}(t)| > THRESHOLD_2$$

The daily difference in long term density estimates are compared to the representative diurnal density estimate assessed following the flattest temperature region:

$$|d_{DR}(t_{BEST}) - d_{LT}(t_{BEsT})| > THRESHOLD_3$$

When one of the above density change triggers occurs, blending models can be invoked to provide a transition in predictive modeling. When slow density changes transpire, thereby avoiding the above triggers occurs, the diurnal and long term processing tracks such slow transitions under the predictive modeling previously described.

Models developed in accordance with the above can be used and/or updated in an ongoing manner, to include after a large step in density such as after a fill. Leak rate projections based on pre-fill modeling after filling can be treated as approximate at the time of fill (but may be accurate, and may be treated as accurate in alternative embodiments), and confidence in the projections can increase as representative daily density estimates become available thereafter. This can be represented by a system of equations. The working density constraint:

$$b_w \cdot e^{a_w \cdot ts} = b_r \cdot e^{a_r \cdot ts}$$

Where subscript r denotes real-time or current regression coefficients and where subscript w implies working values during transition.

The working density from the time of the step forward can match the best current estimate. Until a representative diurnal estimate is available, this value can be used and treated as the real time density. As representative diurnal samples accrue, this will be the density predicted by the evolving regression analyses.

Transition working rate constraint:

$$a_w = \alpha \cdot a_r + (1 - \alpha) \cdot a_{PRESTEP}$$

Transition rate weighting parameter:

$$\alpha = \frac{days}{N}$$

Where α is a fraction increasing toward unity over a programmed number of days N.

The working density decline rate can be modeled as a smooth transition between the last PRESTEP (e.g., before filling) rate and the rate determined by the evolving regression analyses. The parameter a is a fraction increasing toward unity over a programmed number of days N. In embodiments, N can be in a range of 10 to 30 days.

Transition coefficients a, and $b_w$ can be computed in view of these constraints as follows:

$$b_w = b_r \cdot e^{-ts \cdot (aPRESTEP - \alpha \cdot aPRESREP + \alpha \cdot a_r)} \cdot e^{a_r \cdot ts}$$

$$a_w = a_{PRESTEP} - \alpha \cdot a_{PRESTEP} + \alpha \cdot a_r$$

Once N days have elapsed from the time of the density step, the system can proceed based on current regression analyses. In embodiments, the PRESTEP analyses can be disregarded.

The results of the processing described above and other activity can be presented in one or more user interfaces. User interfaces can, but need not, include a variety of possible elements.

One such element can be a temperature corrected pressure gauge. This gauge tracks real-time density and can also track the state of other elements such as, e.g., contacts in a gas-filled breaker. Because of temperature disparities between a given sensor and the gas, real time density and contact indications can vary significantly from actual gas density states. The gauge can include not only real-time displays but also long-term density estimates, e.g. as supplemental overlays, digital readouts, needles or other indicia, et cetera. Further, confidence levels can be indicated with the estimates, e.g., based on color, size, additional displayed readouts, et cetera. In embodiments, lower confidence estimates can be shown as larger illustrative elements covering a range of possible estimates rather than a precise, point (or narrow range) estimate. In embodiments, the estimates of future density can be offset from a real time value at any given time based on instantaneous temperature due to immediate environmental conditions.

Another such element can be a device summary panel which conveys instantaneous conditions of sensor temperature and gas pressure. This panel or display can additionally include various density estimates and associated confidences, as well as the state of various elements such as, e.g., breaker contacts.

Another element can be an application configuration panel which can accept or provide various parameters for entry or display such as gas reference temperature, operating range(s), alarm pressure or range, lockout pressure or range, and others. Gas or container volume (in, e.g., cubic meters) can be calculated based on (or discovering discrepancies in reference to) nameplate capacity or other parameters. Atmospheric pressure and other parameters can also be accepted and/or provided. These and other parameters can be programmable manually or automatically updated based on sensor readings, and can have standard or defaults values (e.g., default pressures as defined by the National Institute of Standards and Technology or other standards organizations).

Another element can be a leak detection panel. Programmable parameters can define one or more daily time ranges (e.g., begin time(s) to end time(s)) during which data is evaluated to find periods of temperature stability or predictability from which representative diurnal density estimates can be produced. Diurnal density estimates can be plotted as points on a graph for display in a leak detection panel or other portion of a user interface. Various regression points can be utilized for exponential regression for display of a trend line in the panel. In addition to displaying the trend line and other data, coefficients a, r, and other variables can be displayed. Time to alarm, time to lockout, and other events or times can be predicted and displayed as well. The actual or nameplate capacity can be used to estimate leak rate (in, e.g., grams per day) and annual leak rate (e.g., grams per year, percentage of total volume, others). In embodiments, distinct alarms or other notifications can be provided if the leak rate exceeds a threshold (e.g., Environmental Protection Agency target of one percent of nameplate capacity annually).

Various sensors can be employed and integrated to provide information herein. In an embodiment, Applicant's 2TC Smart Switch can function as a sensor for producing information relevant to high accuracy gas density estimation, but other sensors or combinations of sensors can be employed without departing from the scope or spirit of the innovation. In various embodiments illustrated herein, other possible sensors or combinations of equipment are shown. In embodiments, drawings provided herewith and described herein can comprise sensors distinct from Applicant's 2TC Smart Switch, or may employ such in a larger system.

Auto-fill devices disclosed herewith can be utilized in accordance with the techniques disclosed above as well, and be used to improve efficiency in real-world systems.

In an embodiment, gas density estimates can provide a time to auto-fill and a time to fill reservoir exhaustion (e.g., when the system is no longer capable of automatically filling or refilling to a target gas density based on a lack of gas available from any or all gas sources). In an embodiment, notifications or alarms can be provided to indicate auto-fill activity and/or predicted exhaustion. These notifications can also influence the timing of low-level alarm or lockout, and in embodiments estimations with and without auto-fill can be provided via interfaces.

Auto-fill activity can be keyed to, e.g., gas density levels. In an embodiment, auto-fill components dose the gas enclosure (e.g., circuit breaker) with additional gas (e.g., SF6) when densities fall below an auto-fill threshold. In embodiments, the auto-fill threshold is greater than or equal to an alarm threshold or lockout threshold. In alternative or complementary embodiments, the auto-fill threshold can also be constrained below an overpressure threshold. Dosing can be sourced from one or more of an internal reservoir, an external reservoir, or a line to a remote reservoir.

Auto-fill thresholds or operating ranges can be defined to increase efficiency as well. As discussed above, leak rate can vary based on a variety of parameters. By identifying these parameters, values for the parameters minimizing leak rates can be imposed on the system. For example, leak rates may be lower at lower density or pressure. However, the gas density must also be kept in an operating range having a minimum gas density to achieve the solution (e.g., avoiding arcing within a breaker). Avoidance of falling below the operating range indicates that, post-fill, the gas density should be provided above the minimum so operation can continue for a length of time in the presence of slow leaks. With the introduction of an auto-fill, though, a lower gas density or pressure closer to the "bottom" of the operating range can be maintained using smaller, more frequent fills to reduce leak rate while keeping gas density within the desired operating range. Because the auto-fill is on-site and obviates human operator collocation, frequent and small fills can be efficiently completed.

In an example embodiment, gas density is monitored in a fluid enclosure (e.g., circuit breaker). An operating range having at least a lower bound for gas density can be established. Gas leaks can be detected and modeled in accordance with aspects herein. In the presence of a gas leak, as the gas density approaches the lower bound, a signal or command can be generated to trigger an auto-fill assembly to increase the gas density by providing more gas from an internal or external reservoir. In embodiments, this can be done by "dosing" the gas, providing discrete, measured increments of gas to avoid over-filling, allow gas density levels to be determined before adding additional gas using the auto-fill, and prevent contamination of the gas reservoir(s). The trigger instruction can be produced or transmitted based on a variety of specific conditions, to include gas density reaching a lower bound, gas density approaching a lower bound based on percentage or absolute density, pre-programmed scheduled dosing based on known or predicted leak rates, dynamic dosing based on actual detected leak rates, et cetera. The trigger causes electromechanical action among one or more actuators, valves, switches, et cetera, to open and close a conduit from the reservoir and permit introduction of additional gas into the fluid enclosure.

Figure 21:
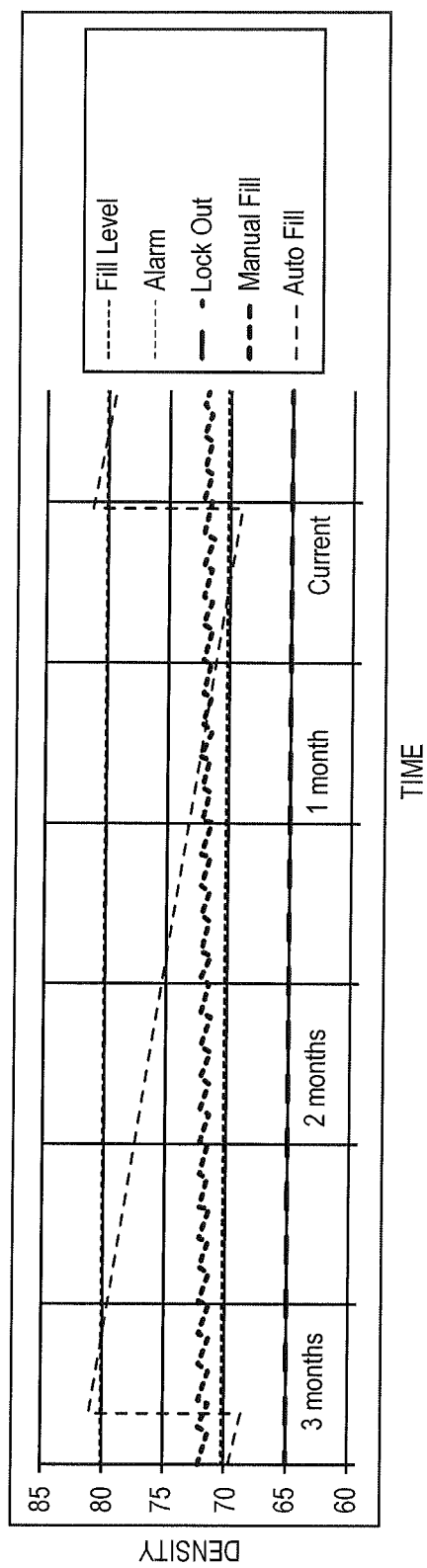
FIG. 21 illustrates an example graph comparing auto-fill embodiments to manual-fill technology.

In this regard, FIG. 21 illustrates an example graph showing gas densities over time using manual fill on one curve and auto-fill on the other. The manual fill shows the impact of a slow, steady leak over months, necessitating a significant re-fill. Because the re-fills raise the gas density to a higher level, in this embodiment the leak rate is also increased, resulting in a higher cost in both labor and lost gas over time. By comparison, the auto-fill embodiment makes small, regular doses to counteract the slow leak, resulting in the gas density level remaining stable above the lockout threshold while increasing predictability regarding the leak rate (and, in embodiments, reducing the overall leak rate) due to sustained operation without density peaks and valleys.

Figure 22:
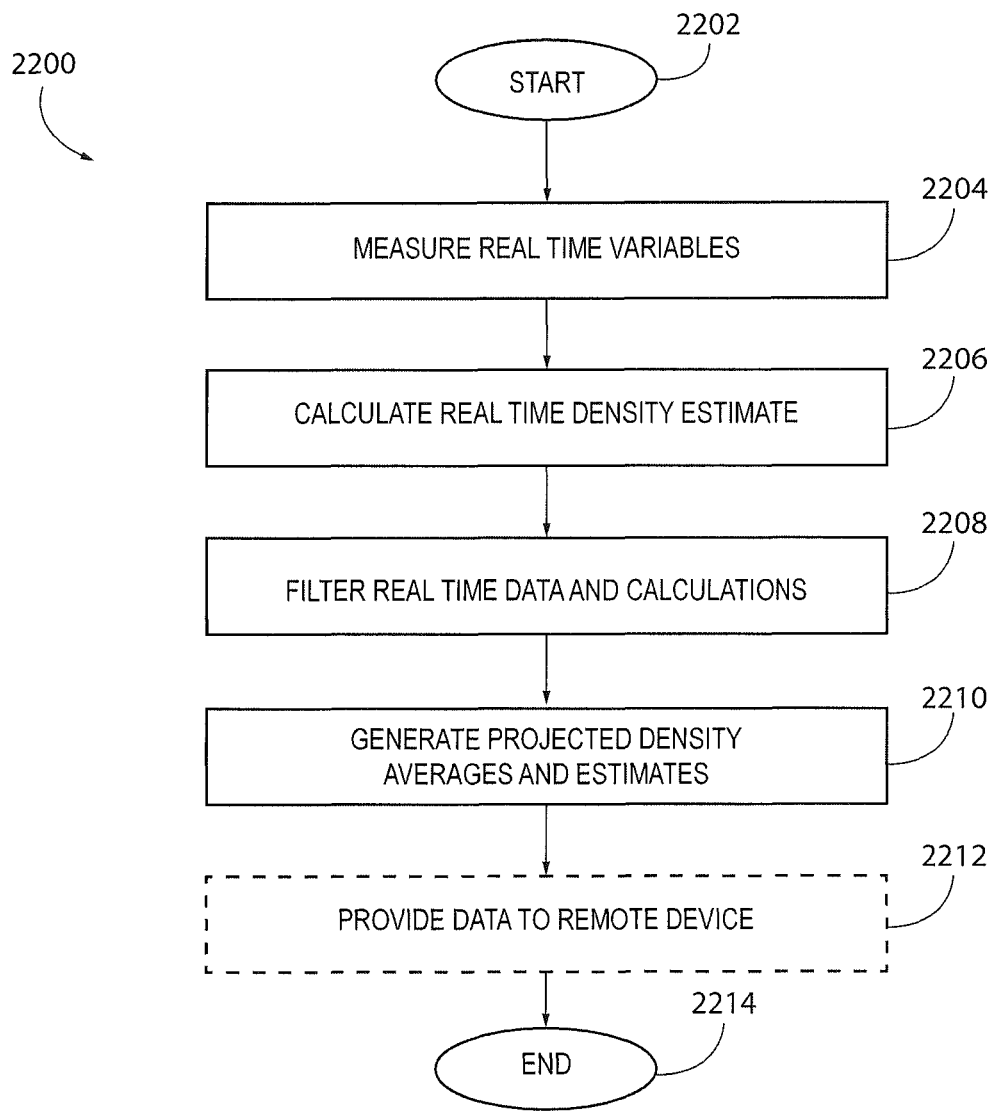
FIG. 22 illustrates an example methodology for monitoring a gas density level.

FIG. 22 illustrates an example methodology 2200 for monitoring a gas density level. Methodology 2200 begins at 2202 and proceeds to 2204 where variables are measured in real time. At 2206 a real time density estimate can be calculated. Thereafter, at 2208, the real time sensed data and calculations can be filtered using techniques described herein. At 2210 projected averages and estimates regarding gas density and other variables can be generated in various time frames (e.g., short term, diurnal, long term, terms therebetween, et cetera). Thereafter, in particular embodiments, the data can be provided to a user interface at 2212. At 2214, methodology 2200 ends, but in embodiments may recycle to provide continuously updating information to the user interface. In an embodiment, the fluid enclosure monitored is a circuit breaker filled at least in part with SF6 gas.

Figure 23:
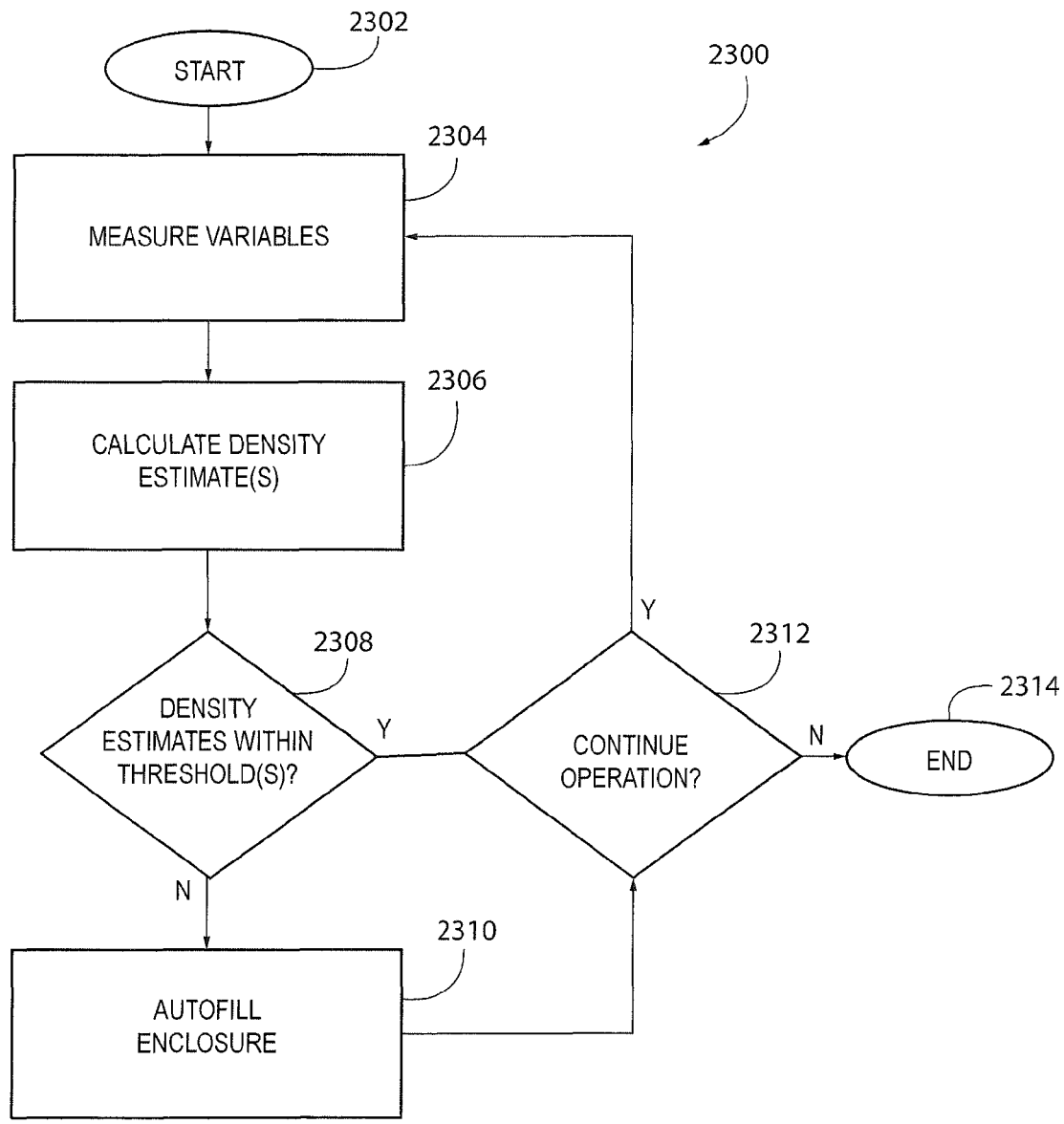
FIG. 23 illustrates an example methodology for maintaining a gas density level.

FIG. 23 illustrates an example methodology 2300 for maintaining a gas density level. Methodology 2300 begins at 2302 and proceeds to 2304 where variables are measured. At 2306 one or more density estimates are calculated in one or more time frames. Once density estimates are known in the immediate or at a future time, a determination is made as to whether such density estimates are within thresholds related to the operating range for the fluid enclosure being monitored and maintained. If the density estimates have departed from the threshold(s) established, the determination at 2308 returns in the negative, and methodology 2300 proceeds to 2310 where the fluid enclosure is auto-filled to restore the density to the desired range. This can occur immediately or be scheduled based on projected density estimates. Thereafter, or if the determination at 2308 returns positive, methodology 2300 proceeds to 2312 where a determination is made as to whether methodology 2300 should continue. If the determination at 2312 returns in the affirmative, methodology 2300 recycles to 2304 and continues to monitor variables and determine auto-fill times. If the determination at 2312 provides a negative response, methodology 2300 proceeds to 2314 and terminates. In an embodiment, the fluid enclosure monitored is a circuit breaker filled at least in part with SF6 gas.

While aspects herein may at times tend toward the management of sulfur hexafluoride levels in circuit breakers, it is understood that systems and methods herein can be applied to other environments as well.

In the specification and claims, reference will be made to a number of terms that have the following meanings. The singular forms "a", "an" and "the" include plural referents unless the context clearly dictates otherwise. Approximating language, as used herein throughout the specification and claims, may be applied to modify a quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Moreover, unless specifically stated otherwise, a use of the terms "first," "second," etc., does not denote an order or importance, but rather the terms "first," "second," etc., are used to distinguish one element from another.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable, or suitable. For example, in some circumstances an event or capacity can be expected, while in other circumstances the event or capacity cannot occur—this distinction is captured by the terms "may" and "may be."

This written description uses examples to disclose the invention, including the best mode, and also to enable one of ordinary skill in the art to practice the invention, including making and using devices or systems and performing incorporated methods. The patentable scope of the invention is defined by the claims, and may include other examples that occur to one of ordinary skill in the art. Such other examples are intended to be within the scope of the claims if they have structural elements that do not differentiate from the literal language of the claims, or if they include equivalent structural elements with insubstantial differences from the literal language of the claims.

What is claimed is:

1. A system for monitoring fluid in a fluid enclosure filled at least in part with a fill gas, the system comprising:
   a temperature probe in sensing communication with the fluid enclosure configured to receive at least an enclosure temperature from the fluid enclosure and provide a temperature signal;
   an atmospheric pressure sensor in sensing communication with an environment around the fluid enclosure configured to monitor at least an atmospheric pressure and to generate a pressure signal;
   a gas sensor in sensing communication with the fluid enclosure that monitors at least an enclosure pressure within the fluid enclosure and configured to generate an enclosure gas pressure signal; and
   a controller in electrical communication with the temperature probe, atmospheric pressure sensor, gas sensor and configured to receive signals therefrom,
   wherein the controller is configured to compute a fill gas density within the fluid enclosure based at least in part on the enclosure temperature, the atmospheric pressure, the enclosure pressure, and a gas coefficient of the fill gas; an auto-fill assembly in communication with the controller; and
   a gas source of the auto-fill assembly in fluid communication with the fluid enclosure, wherein the auto-fill assembly is configured to provide additional fill gas to the fluid enclosure from the gas source upon receiving a signal from the controller and
   the controller is further configured to trigger the auto-fill assembly based at least in part on the fill gas density.

2. The system of claim 1, the controller is further configured to provide at least data for a user interface displaying at least one of the enclosure temperature, the atmospheric pressure, the enclosure pressure, and the fill gas density.

* * * * *